US00RE47300E

(19) United States
(12) Reissued Patent
Ralph et al.

(10) Patent Number: US RE47,300 E
(45) Date of Reissued Patent: Mar. 19, 2019

(54) MITOCHONDRIALLY DELIVERED ANTI-CANCER COMPOUNDS

(71) Applicant: Cancure Limited, Southport (AU)

(72) Inventors: Stephen John Ralph, Mermaid Waters (AU); Jiri Neuzil, Runaway Bay (AU)

(73) Assignee: CANCURE LIMITED, Southport, Queensland (AU)

(21) Appl. No.: 14/955,297

(22) Filed: Dec. 1, 2015

Related U.S. Patent Documents

Reissue of:
(64) Patent No.: 8,598,145
Issued: Dec. 3, 2013
Appl. No.: 12/922,525
PCT Filed: Mar. 16, 2009
PCT No.: PCT/AU2009/000312
§ 371 (c)(1),
(2) Date: Dec. 10, 2010
PCT Pub. No.: WO2009/000312
PCT Pub. Date: Sep. 17, 2009

(30) Foreign Application Priority Data

Mar. 14, 2008 (AU) ..... 2008901261

(51) Int. Cl.
*C07F 9/655* (2006.01)
*C07D 311/72* (2006.01)
(Continued)

(52) U.S. Cl.
CPC ..... *C07F 9/65522* (2013.01); *A61K 31/355* (2013.01); *A61K 47/54* (2017.08); *A61K 47/551* (2017.08); *C07D 311/72* (2013.01)

(58) Field of Classification Search
CPC ..... A61K 31/355; A61K 47/48107; A61K 47/48023; C07D 311/72; C07F 9/65522
(Continued)

(56) References Cited

U.S. PATENT DOCUMENTS 6,331,532 B1 * 12/2001 Murphy et al. ..... 514/100
8,410,056 B2 4/2013 Ralph et al.
2003/0069208 A1 4/2003 Murphy et al.

FOREIGN PATENT DOCUMENTS

CA 2536546 A1 3/2005
WO WO-2005/019232 A1 3/2005
(Continued)

OTHER PUBLICATIONS

Albayrak et al., "The tumor suppressor cybL, a component of the respiratory chain, mediates apoptosis induction", *Molecular Biology of the Cell*, 14:3082-96 (2003).
(Continued)

*Primary Examiner* — Sharon Turner
(74) *Attorney, Agent, or Firm* — Marshall, Gerstein & Borun LLP

(57) ABSTRACT

This invention relates to anti-cancer compounds and to methods for treating or preventing cancer. In one aspect the invention concerns mitochondrially delivered pro-oxidant anti-cancer compounds that generate reactive oxygen species and induce apoptosis of cancerous cells. The delivery moiety can be a lipophilic cation and the pro-oxidant moiety can be a pro-oxidant vitamin E analogue, such as α-tocopheryl succinate, α-tocopheryl maleate, α-tocopheryl maleyl amide, or 2,5,7,8-tetramethyl-2R-(4R,8R,12-trimethyltridecyl)-chroman-6-yloxyacetic acid (α-tocopheryloxyacetic acid).

18 Claims, 9 Drawing Sheets

(51) Int. Cl.
*A61K 47/55* (2017.01)
*A61K 47/54* (2017.01)
*A61K 31/355* (2006.01)

(58) Field of Classification Search
USPC ..... 514/100
See application file for complete search history.

(56) References Cited

FOREIGN PATENT DOCUMENTS

| | | | |
|---|---|---|---|
| WO | WO-2006/015120 | A2 | 2/2006 |
| WO | WO-2006/094203 | A1 | 9/2006 |
| WO | WO-2007/046729 | A1 | 4/2007 |
| WO | WO-2008/145116 | A2 | 12/2008 |

OTHER PUBLICATIONS

Arya et al., "Design and synthesis of analogues of vitamin E:antiproliferative activity against human breast adenocarcinoma cells", *Bioorg. Med. Chem. Lett.*, 8:2433-8 (1998).
Baysal et al., "Mutations in SDHD, a mitochondrial complex II gene, in heredity paraganglioma", *Science*, 287(5454):848-51 (2000).
Birringer et al., "Vitamin E analogues as inducers of apoptosis: structure-function relationship", *Br. J. Cancer*, 88:1948-55 (2003).
Constantinou et al., "Vitamin E and cancer: An insight into the anticancer activities of vitamin E isomers and analogs", *Int. J. Cancer*, 123(4):739-52 (2008).
Dong et al., "Vitamin E analogs inhibit angiogenesis by selective apoptosis induction in proliferating endothelial cells: The role of oxidative stress", *Cancer Res.*, 67:11906-13 (2007).
Eyler et al., "Survival of the fittest: cancer stem cells in therapeutic resistance and angiogenesis", *J. Clin. Oncol.*, 26(17):2839-45 (2008).
Farnie et al., "Novel cell culture technique for primary ductal carcinoma in situ: role of notch and epidermal growth factor receptor signaling pathways", *J. Natl. Cancer Inst.*, 99(8):616-27 (2007).
Galli et al., "The effect of α- and γ-tocopherol and their carboxymethyl hydroxychroman metabolites on prostate cancer cell proliferation", *Arch. Biochem. Biophys.*, 423:97-102 (2004).
Grimshaw et al., "Mammosphere culture of metastatic breast cancer cells enriches for tumorigenic breast cancer cells", *Breast Cancer Res.*, 10(3):R52 (2008).
Guthrie et al., "Inhibition of proliferation of estrogen receptor-negative MDA-MB-435 and positive MCF-7 human breast cancer cells by palm oil tocotrienols and tamoxifen, alone and in combination", *J. Nutr.*, 127:544S-548S (1997).
Guzman et al., "Rapid and selective death of leukemia stem and progenitor cells induced by the compound 4-benzyl, 2-methyl, 1,2,4-thladiazolidine, 3,5 dione (TDZD-8)", *Blood*, 110(13):4436-44 (2007).
Guzman et al., "The sesquiterpene lactone parthenolide induces apoptosis of human acute myelogenous leukemia stem and progenitor cells", *Blood*, 105(11):4163-9 (2005).
He et al., "Isoprenoids suppress the growth of murine B16 melanomas in vitro and in vivo",*J. Nutr.*, 127:668-74 (1997).
He et al., "Protein ubiquinone interaction. Synthesis and biological properties of 5-alkyl ubiquinone derivatives", *J. Biol. Chem.*, 269(45): 27885-8 (1994).
Hsu et al., "Green tea polyphenol targets the mitochondria in tumor cells inducing caspase 3-dependent apoptosis", *Anticancer Res.*, 23(2B):1533-9 (2003).
Kogure et al., "Cytotoxicity of α-tocopheryl succinate, malonate and oxalate in normal and cancer cells in vitro and their anti-cancer effects on mouse melanoma in vivo", *J. Nutr. Sol. Vitaminol.*, 51:392-7 (2005).
Kogure et al., "Structural characteristic of terminal dicarboxylic moiety required for apoptogenic activity of α-tocopheryl esters", *Biochim. Biophys. Acta.*, 1672:93-99 (2004).
Kumagai et al., "The structures of atpenins A4, A5 and B, new antifungal antibiotics produced by *Penicillium sp", J. Antibiot.* (Tokyo), 43(12):1553-8 (2009).
Kurtoglu et al., "From delocalized lipophilic cations to hypoxia: blocking tumor cell mitochondrial function leads to therapeutic gain with glycolytic inhibitors", *Mol. Nutr. Food Res.*, 53(1):68-75 (2009).
Lahouel et al., "Ferulenol specifically inhibits succinate ubiquinone reductase at the level of the ubiquinone cycle", *Biochem. Biophys. Res. Commun.*, 355(1):252-7 (2007).
Li et al., "Intrinsic resistance of tumorigenic breast cancer cells to chemotherapy", *J. Natl. Cancer Inst.*, 100(9):672-9 (2008).
Lou et al., "Targeted therapy for cancer stem cells: the patched pathway and ABC transporters", *Oncogene*, 26(9):1357-60 (2007).
Makishima et al., "Induction of differentiation in acute promyelocytic leukemia cells by 9-cis retinoic acid α-tocopherol ester (9-cis tretinoin tocoferil)", *Blood*, 91:4715-26 (1998).
Modica-Napolitano et al., "Delocalized lipophilic cations selectively target the mitochondria of carcinoma cells", *Adv. Drug Deliv. Rev.*, 49(1-2):63-70 (2001).
Munteanu et al., "Modulation of cell proliferation and gene expression by α-tocopheryl phosphates: relevance to atherosclerosis and inflammation", *Biochem. Biophys. Res. Commun.* 318:311-6 (2004).
Murphy et al., "Targeting antioxidants to mitochondria by conjugation to lipophilic cations", *Annu. Rev. Pharmacol. Toxicol.*, 47:629-56 (2007).
Nesaretnam et al., "Tocotrienols inhibit the growth of human breast cancer cells irrespective of estrogen receptor status", *Lipids*, 33:461-9 (1998).
Neuzil et al. "Molecular mechanism of 'mitocan'-induced apoptosis in cancer cells epitomizes the multiple roles of reactive oxygen species and Bcl-2 family proteins", *FEBS Letters*, 580:5125-9 (2006).
Neuzil et al., "α-Tocopheryl succinate, an agent with in vivo anti-tumour activity, induces apoptosis by causing lysosomal instability", *Biochem J.*, 362:709-15 (2002).
Neuzil et al., "Induction of apoptosis in cancer cells by α-tocopheryl succinate: molecular pathways and structural requirements", *FASEB J.*, 15:403-15 (2001).
Neuzil et al., "Selective cancer cell killing by α-tocopheryl succinate", *Br. J. Cancer*, 84:87-9 (2001).
Neuzil et al., "Tumour-initiating cells vs. cancer 'stem' cells and CD133: what's in the name?", *Biochem. Biophys. Res. Commun.*, 355(4):855-9 (2007).
Neuzil et al., "Vitamin E analogs, a novel group of 'mitocans', as anti-cancer agents: The importance of being redox-silent", *Mol. Pharmacol.*, 71:1185-99 (2007).
O'Brien et al., "Are stem-like cells responsible for resistance to therapy in breast cancer?", *Breast Dis.*, 29:83-9 (2008).
Phillips et al., "The response of CD24-/low/CD44+ breast cancer-initiating cells to radiation", *J. Natl. Cancer Inst.*, 98(24):1777-85 (2006).
Shah et al., "γ-Tocotrienol inhibits neoplastic mammary epithelial cell proliferation by decreasing Akt and nuclear factor KB activity", *Exp. Biol. Med.*, 230:235-41 (2005).
Shiau et al., "α-Tocopheryl succinate induces apoptosis in prostate cancer cells in part through inhibition of Bcl-xL/Bc1-2 function", *J. Biol. Chem.*, 281:11819-11825 (2006).
Shun et al., "Pro-apoptotic mechanisms of action of a novel vitamin E analog (α-TEA) and a naturally occurring form of vitamin E (δ-tocotrienol) in MDA-MB-435 human breast cancer cells", *Nutr. Cancer*, 48:95-105 (2004).
Smith et al., "Selective targeting of an antioxidant to mitochondria", *Eur. J. Biochem.*, 263:709-16 (1999).
Sotiriou et al., "Gene-expression signatures in breast cancer", *N. Engl. J. Med.*, 360(8):790-800 (2009).
Stapelberg et al., "α-Tocopheryl succinate inhibits malignant mesothelioma by disrupting the FGF autocrine loop: The role of oxidative stress", *J. Biol. Chem.*, 280:25369-76 (2005).
Swettenham et al., "α-Tocopheryl succinate selectively induces apoptosis in neuroblastoma cells: Potential therapy of malignancies of the nervous system?", *J. Neurochem.* 94:1448-56 (2005).

(56) References Cited

OTHER PUBLICATIONS

Sørlie et al., "Gene expression patterns of breast carcinomas distinguish tumor subclasses with clinical implications", *Proc. Natl. Acad. Sci. USA.*, 98(19):10869-74 (2001).
Tomasetti et al. "α-Tocopheryl succinate induces DR4 and DR5 expression by a p53-dependent route: implication for sensitisation of resistant cancer cells to TRAIL apoptosis", *FEBS Lett.*, 580:1925-31 (2006).
Tomasetti et al., "A vitamin E analogue suppresses malignant mesothelioma in a pre-clinical model: A prototype of a future drug against a fatal neoplastic disease?", *Int. J. Cancer*, 109:641-2 (2004).
Tomic-Vatic et al., "Vitamin E amides, a new class of vitamin E analogues with enhanced pro-apoptotic activity", *Int. J. Cancer*, 117:118-93 (2005).
Vraka et al., "Synthesis and study of the cancer cell growth inhibitory properties of (α-, γ-tocoptieryl and γ-tocotrienyl 2-phenylselenyl succinates", *Bioorg. Med. Chem.*, 14:2684-96 (2006).
Wang et al., "α-Tocopheryl succinate induces apoptosis in HER2/erbB2-overexpressing breast cancer cells by signalling via the mitochondrial pathway", *Biochem. Biophys. Res. Commun.*, 326:282-9 (2004).
Wang et al., "A peptide conjugate of vitamin E succinate targets breast cancer cells with high erbB2 expression", *Cancer Res.*, 67:3337-44 (2007).
Wang et al., "Vitamin E analogs trigger apoptosis in HER2/erbB2-overexpressing breast cancer cells by signaling via the mitochondrial pathway", *Biochem. Biophys. Res. Commun.*, 326(2): 282-9 (2005).
Weber et al., "Mitochondria play a central role in apoptosis induced by α-tocopheryl succinate, an agent with anticancer activity. Comparison with receptor-mediated pro-apoptotic signaling", *Biochemistry*, 42:4277-91 (2003).
Weber et al., "Vitamin E succinate is a potent novel anti-neoplastic agent with high tumor selectivity and cooperativity with tumor necrosis factor-related apoptosis-inducing ligand (TRAIL, Apo2L) in vivo", *Clin. Cancer Res.*, 8:863-9 (2002).
Yano et al., "Induction of cytotoxicity in human lung adenocarcinoma cells by 6-O-carboxy-propyl-α-tocotrienol, a redox-silent derivative of α-tocotrienol", *Int. J. Cancer*, 115:839-46 (2005).
Neuzil et al. (FEBS Letters, 580, 2006, 5125-29).*
Smith et al. (Eur J Biochem. 263, 709-16, 1999).*

* cited by examiner (New)

1 = mitoVS
2 = VS
3 = VS + mitoQ
4 = mitoQ

MITOCHONDRIALLY DELIVERED ANTI-CANCER COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

This invention relates, inter alia, to anti-cancer compounds and to methods for treating or preventing cancer. In particular, the invention concerns mitochondrially delivered pro-oxidant anti-cancer compounds that generate reactive oxygen species and induce apoptosis of cancerous cells.

BACKGROUND OF THE INVENTION

With the advance in molecular medicine, our understanding of molecular biology of cancer initiation, progression and treatment have improved, resulting in better therapeutic approaches. However, since a neoplastic cell can be characterised as a de-differentiated normal cell with chromosome instability, novel mutations occur, making established anti-cancer drugs obsolete. Certain malignancies, including malignant mesotheliomas (MMs), cannot be treated at present (Robinson B W, Musk A W, Lake A (2005) Lancet 366, 397-408). Others, such as the HER2-positive breast carcinomas (Piccart-Gebhart M Jet al (2005) N Engl J Med 353, 1659-1672) rely on the very expensive Herceptine™ that shows considerable cardiotoxicity. Thus, new drugs and strategies that would overcome complications of current therapeutic approaches are required.

A novel concept has emerged whereby targeting of mitochondria has become increasingly recognised as a promising and highly effective anti-cancer approach (Don A S, Hogg P J (2004) Trends Mol Med 10, 372-378; Armstrong J S (2007) Br J Pharmacol 151, 1154-1165). The present inventors have recently proposed the term, "mitocans", referring to small molecules with anti-cancer activity that induce apoptosis by destabilizing mitochondria in cancer cells (Neuzil J, Wang X F, Dong L F, Low P, Ralph S J (2006) FEBS Lett 580, 5125-5129; Neuzil J et al (2007) J Bioenerg Biomembr 39, 65-72; Neuzil J et al (2007) Mol Pharmacol 71, 1185-1199). The present inventors have grouped these molecules according to their mode of action, as seen in Table I (Neuzil Jet at (2007) Mol Pharmacol 71, 1185-1199).

TABLE I

Classification of mitocans.

| Class | Type | Examples |
|---|---|---|
| I | Hexokinase inhibitors | 3-Bromopyruvate (Ko Y H et al (2004) Biochem Biophys Res Commun 324, 269-275; Xu R H et al (2005) Cancer Res 65, 613-621)<br>2-Deoxyglucose (Ko Y H et al (2004) Biochem Biophys Res Commun 324, 269-275) |
| II | Bcl-2/Bcl-$x_L$ BH3 mimetics | Gossypol (Kitada S et al (2008) Blood (in press))<br>Antimycin A (Tzung S P et al (2001) Nat Cell Biol 3, 183-191)<br>BH3I-2' (Degterev A et al (2001) Nat Cell Biol 3, 173-182)<br>α-Tocopheryl succinate (Shiau C W et al (2006) J Biol Chem 281, 11819-11825) |

TABLE I-continued

Classification of mitocans.

| Class | Type | Examples |
|---|---|---|
| III | Thiol redox inhibitors | Isothiocyanates (PITC) (Xu K, Thornalley P J (2001) Biochem Pharmacol 61, 165-177)<br>Arsenic trioxide (Miller W H (2002) Oncologist 7, S14-19) |
| IV | VDAC/ANT targeting drugs | Lonidamine (Belzacq A S et al (2001) Oncogene 20, 7579-7587)<br>Arsenites (Don A S et al (2003) Cancer Cell 3, 497-509) |
| V | Electron transport chain targeting drugs | 4-OH retinamide (Hail N, Lotan R (2001) J Biol Chem 276, 45614-45621)<br>Tamoxifen (Moreira P I et al (2006) J Biol Chem 281, 10143-10152)<br>Antimycin A (Wolvetang E J, Johnson K L, Krauer K, Ralph S J, Linnane A W (1994) FEBS Lett 339, 40-44)<br>α-Tocophelyl succinate (Dong L F et al (2008) Oncogene (in press)) |
| VI | Lipophilic cations targeting inner membrane | Rhodamine-123 (Lampidis T J, Bernal S D, Summerhayes I C, Chen L B (1983) Cancer Res 43, 716-720)<br>F16 (Fantin V R et al (2002) Cancer Cell 2, 29-42)<br>$(KLAKKLAK)_2$ peptide (Ellerby H M et al (1999) Nat Med 5, 1032-1038) |
| VII | Drugs targeting other sites | Resveratrol (ATPase ?) (Zheng J, Ramirez V D (1999) Biochem Biophys Res Commun 261, 499-503)<br>Betulinic acid (Fulda S et al (1998) J Biol Chem 273, 33942-33948), DCA (Bonnet S et al (2007) Cancer Cell 11, 37-51) |

The list of mitocans currently includes 7 groups, each of them comprising agents with distinct activities, whereby causing mitochondrial destabilisation and the ensuing induction of the intrinsic apoptotic pathway (Neuzil J et al (2007) Mol Pharmacol 71, 1185-1199).

Mitocans are proving to be attractive for the treatment of cancer since some of these compounds are potent and selective anti-cancer agents with little effect on normal cells (Neuzil J et al (2007) Mol Pharmacol 71, 1185-119; Ko Y H et al (2004) Biochem Biophys Res Commun 324, 269-275; Bonnet S et al (2007) Cancer Cell 11, 37-51). Prime examples of such drugs include α-tocopheryl succinate (α-TOS), inducing selective apoptosis of cancer cells (Neuzil J, Weber T, Gellert N, Weber C (2001) Br J Cancer 84, 87-89; Neuzil J et al (2004) Curr Cancer Drug Targets 4, 267-284) as well as 3-bromopyruvate (3BP) (Ko Y H et al (2004) Biochem Biophys Res Commun 324, 269-275; Geschwind J F et al (2002) Cancer Res 62, 3909-3913), dichloroacetate (DCA) (Bonnet S et al (2007) Cancer Cell 11, 37-51) and β-phenylethyl isothiocyanate (PITC) (Trachootham D et al (2006) Cancer Cell 10, 241-252).

3BP inhibits hexokinase, an enzyme of the glycolytic pathway predominantly bound to the external face of mitochondria, and also inhibits the mitochondrial enzyme succinate dehydrogenase (SDH), suppressing cellular ATP production and mitochondrial respiration (Ko Y H et al (2004) Biochem Biophys Res Commun 324, 269-275; Xu R H et al (2005) Cancer Res 65, 613-621).

DCA appears to selectively target cancer cells by inhibiting the mitochondrial pyruvate dehydrogenase kinase (Bonnet S et al (2007) Cancer Cell 11, 37-51). PITC selectively kills cancer cells by causing mitochondrial generation of reactive oxygen species (ROS) (Trachootham D et al (2006) Cancer Cell 10, 241-252). All these examples of mitocans reflect an emerging group of compounds with substantial promise and a new direction for developing improved and highly selective novel anti-cancer drugs.

One group of mitocans includes pro-oxidant analogues of vitamin E (Wang X F, Dong L F, Zhao Y, Tomasetti M, Wu K, Neuzil J (2006) Vitamin E analogues as anti-cancer agents: Lessons from studies with α-tocopheryl succinate. Mol Nutr Food Res 50:675-685). The great promise of pro-oxidant vitamin E analogues, epitomized by α-TOS, as anti-cancer drugs stems from studies with experimentally contrived cancers, such as human xenografts growing in nude mice, where they have been shown to suppress malignancy (reviewed in Neuzil J, Tomasetti M, Mellick A S, Alleva R, Salvatore B A, Birringer M, Fariss M W (2004) Vitamin E analogues: A new class of inducers of apoptosis with selective anti-cancer effects. Curr Cancer Drug Targets 4:355-372). Such studies include colorectal (Neuzil J, Weber T, Gellert N, Weber C (2001) Selective cancer cell killing by α-tocopheryl succinate. Br J Cancer 84:87-89; Neuzil J, Weber T, Schroder A, Lu M, Ostermann G, Gellert N, Mayne G C, Olejnicka B, Negre-Salvayre A, Sticha M, Coffey R J, Weber C (2001) Induction of apoptosis in cancer cells by α-tocopheryl succinate: Molecular pathways and structural requirements. FASEB J 15:403-415; Weber T, Lu M, Andera L, Lahm H, Gellert N, Fariss M W, Korinek V, Sattler W, Ucker D S, Temman A, Schroder A, Erl W, Brunk U T, Coffey R J, Weber C, Neuzil J (2002) Vitamin E succinate is a potent novel anti-neoplastic agent with high tumor selectivity and cooperativity with tumor necrosis factor-related apoptosis-inducing ligand (TRAIL, Apo2L) in vivo. Clin Cancer Res 8:863-869) and lung carcinomas (Quin J, Engle D, Litwiller A, Peralta E, Grasch A, Boley T, Hazelrigg S (2005) Vitamin E succinate decreases lung cancer tumor growth in mice. J Surg Res 127:139-143), melanomas (Malafa M P, Fokum F D, Mowlavi A, Abusief M, King M (2002) Vitamin E inhibits melanoma growth in mice. Surgery 131:85-91), as well as mesotheliomas (Tomasetti M, Gellert N, Procopio A, Neuzil J (2004) A vitamin E analogue suppresses malignant mesothelioma in a pre-clinical model: A prototype of a future drug against a fatal neoplastic disease? Int J Cancer 109:641-642; Stapelberg M, Gellert N, Swettenham E, Tomasetti M, Witting P K, Procopio A, Neuzil J (2005) α-Tocopheryl succinate inhibits malignant mesothelioma by disruption of the FGF autocrine signaling loop: Mechanism and the role of oxidative stress. J Biol Chem 280:25369-25376). α-TOS has also been shown to promote breast cancer dormancy (Malafa et al, 2000) and suppress colon cancer metastases into the liver (Barnett K T, Fokum F D, Malafa M P (2002) Vitamin E succinate inhibits colon cancer liver metastases. J Surg Res 106:292-298).

Although vitamin E (α-tocopherol, α-TOH) acts as a potent anti-oxidant in cells, α-TOS, an esterified, redox-silent and pro-oxidant analogue of vitamin E, has distinctive properties. In contrast to α-TOH, α-TOS acts as a strong cell stressor, causing rapid production of ROS in a range of different cancer cell lines (Neuzil J, Tomasetti M, Mellick A S, Alleva R, Salvatore B A, Birringer M, Fariss M W (2004) Vitamin E analogues: A new class of inducers of apoptosis with selective anti-cancer effects. Curr Cancer Drug Targets 4:355-372; Weber T, Dalen H, Andera L, Negre-Salvayre A, Auge N, Sticha M, Lloret A, Terman A, Witting P K, Higuchi M, Plasilova M, Zivny J, Gellert N, Weber C, Neuzil J (2003) Mitochondria play a central role in apoptosis induced by α-tocopheryl succinate, an agent with anticancer activity. Comparison with receptor-mediated pro-apoptotic signaling. Biochemistry 42:4277-4291; Wang X F, Witting P K, Salvatore B A, Neuzil J (2005) α-Tocopheryl succinate induces apoptosis in HER2/erbB2-overexpressing breast cancer cells by signalling via the mitochondrial pathway. Biochem Biophys Res Commun 326:282-289; Swettenham E, Witting P K, Salvatore B A, Neuzil J (2005) α-Tocopheryl succinate selectively induces apoptosis in neuroblastoma cells: Potential therapy of malignancies of the nervous system? J Neurochem 94:1448-1456; Stapelberg M, Gellert N, Swettenham E, Tomasetti M, Witting P K, Procopio A, Neuzil J (2005) α-Tocopheryl succinate inhibits malignant mesothelioma by disruption of the FGF autocrine signaling loop: Mechanism and the role of oxidative stress. J Biol Chem 280:25369-25376). α-TOS also has the ability to bind to and inhibit Bcl-2/Bcl-xL (Dong L F, Wang X F, Zhao Y, Tomasetti M, Wu K, Neuzil J (2006) Vitamin E analogues as anti-cancer agents: the role of modulation of apoptosis signalling pathways. Cancer Therapy 4:35-46). Evidence to date suggests that the cancer cell-specific nature of α-TOS and the lack of toxic effect on normal cells occurs because normal cells are endowed with greater anti-oxidant defenses (Allen R G, Balin A K (2003) Effects of oxygen on the antioxidant responses of normal and transformed cells. Exp Cell Res 289:307-316; Safford S E, Oberley T D, Urano M, St Clair D K (1994) Suppression of fibrosarcoma metastasis by elevated expression of manganese superoxide dismutase. Cancer Res 54:4261-4265; Church S L, Grant J W, Ridnour L A, Oberley L W, Swanson P E, Meltzer P S, Trent J M (1993) Increased manganese superoxide dismutase expression suppresses the malignant phenotype of human melanoma cells. Proc Natl Acad Sci USA 90:3113-3117) and/or contain high levels of esterases that inactivate α-TOS by releasing the succinate moiety, thereby producing the redox-active, non-apoptogenic α-TOH (Fariss M W, Nicholls-Grzemski F A, Tirmenstein M A, Zhang J G (2001) Enhanced antioxidant and cytoprotective abilities of vitamin E succinate is associated with a rapid uptake advantage in rat hepatocytes and mitochondria. Free Radic Biol Med 31:530-541; Neuzil J, Tomasetti M, Mellick A S, Alleva R, Salvatore B A, Birringer M, Fariss M W (2004) Vitamin E analogues: A new class of inducers of apoptosis with selective anti-cancer effects. Curr Cancer Drug Targets 4:355-372; Neuzil J, Massa H (2005) Hepatic processing determines dual activity of vitamin E succinate. Biochem Biophys Res Commun 327:1024-1027).

Naturally occurring vitamin E consists of a mixture of eight compounds which differ by the methylation patterns of the chromanol ring (α-, β-, γ-, δ-tocopherol) and the number of double bonds of the phytyl side-chain (α-, β-, γ, δ-tocotrienol). The role of these molecules as lipophilic anti-oxidants in vitro and in vivo is widely accepted. In addition, the non-anti-oxidant properties of members of the VE family have also been investigated (Azzi A, Ricciarelli R and Zingg J M (2002) Non-antioxidant molecular functions of α-tocopherol (vitamin E). FEBS Lett 519:8-10).

The vitamin E molecule can be divided into three different domains. The Functional Domain (I) arises from the substitution pattern at position C6 of the chromanol ring. This position determines whether the molecule behaves as redox-active or redox-silent, since a free hydroxyl group is essential for vitamin E to function as an anti-oxidant. The well documented anti-oxidant properties of the four tocopherol isomers resulted in their application in cancer clinical trials. None of these studies showed a positive outcome concerning the use of free tocopherols in cancer prevention (Pham DQ and Plakogiannis R (2005) Vitamin E supplementation in cardiovascular disease and cancer prevention: Part 1. Ann Pharmacother 39:1870-8). However, certain chemical modifications at C6 led to ethers (RO—), esters (RCOO—) and amides (RCONH—) that proved to be potent anti-neoplastic agents. See Table II below.

TABLE II

Anti-proliferative activity of vitamin E analogues.
Compounds are sorted by the Signaling Domain.

| Nr | Functional Domain I (R1) | Signalling Domain II | Hydrophobic Domain III (R2) | $IC_{50}$ [μM] | Cell type | Ref (see the list of refs) |
|---|---|---|---|---|---|---|
| 1 | $^{-}O_2CCH_2CH_2COO$— | 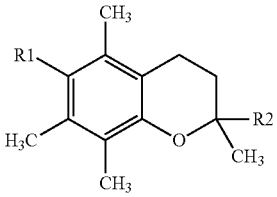 | 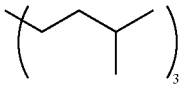 | 43 | Jurkat, | Birringer |
| 2 | $CH_3COO$— | | | [a] | HBT11, | et al, |
| 3 | $^{-}O_2CCH{=}CHCOO$— | | | 22 | MCF7, | 2003 |
| 4 | $^{-}O_2CCH_2CH(CH_3)COO$— | | | [b] | MCF7-C3 | |
| 5 | $^{-}O_2CCH_2(CH_2)_2COO$— | | | [b] | | |
| 6 | $^{-}O_2CCH_2CH(CH_3)CH_2COO$— | | | [b] | | |
| 7 | $^{-}O_2CCH_2C(CH_3)_2CH_2COO$— | | | [b] | | |
| 8 | $^{-}O_2CCH(CH_3)_2CH_2CH_2COO$— | | | [b] | | |
| 9 | $H_3COOCCH_2CH_2COO$— | | | [b] | | |
| 10 | $^{-}O_2CCOO$— | | | [c] | B16-F1/ | Kogure |
| 11 | $^{-}O_2CCH_2COO$ | | | | nude | et a., |
| | | | | | mice | 2005 |
| 12 | $^{-}O_2CCH_2CH_2CONH$— | | | 13 | Jurkat, | Tomoc- |
| 13 | $^{-}O_2CCH{=}CHCONH$— | | | 2 | U937, | Vatic et |
| 14 | $H_3COOCCH_2CH_2CONH$— | | | >100 | Meso-2 | al, 2005 |
| 15 | $^{+}NH_3$—$CH_2COO$— | | | [a] | MCF7 | Arya et |
| 16 | $^{+}NH_3Lys(NH_3)COO$— | | | 12 | | al, 1995 |
| 17 | Lys-Lys(Lys)COO— | | | [a] | | |
| 18 | $CH_3O$— | | | [a] | Jurkat | Neuzil et al, 2001b |
| 19 | $CH_3CH_2COO$— | | | [d] | A549 | Yano et al, 2005 |
| 20 | $^{-}O_2CCH_2CH_2CH_2O$— | | | [e] | LNCa P, PC-3 MDA-MB-453 | Wu et al, 2004; Nishika wa et al, 2003 |
| 21 | $^{-}O_2CCH_2O$— | | | [f] | MDA-MB-435, MCF7 | Shun et al, 2004 |
| 22 | $^{-}O_2CCH_2$— | | | 15-20[g] | MCF7 | Shiau et al, 2006 |
| 23 | (PEG)$O_2CCH_2CH_2COO$— | | | [h] | lung carcinoma cells/ nude mice | Youk et al, 2005 |
| 24 | $^{-}O_2C(CH_2)_5COO$— | | | [a] | C127I | Kogure |
| 25 | $C_2H_5OOCCH_2CH_2COO$— | | | [a] | | et al, |
| 26 | nicotinic acid | | | [a] | | 2004 |
| 27 | $^{-}O_2CCH_2CH(SePh)COO$— | | | ? | prostate | Vraka et al, 2006 |
| 28 | all-trans retinoic acid | | | 0,1-1 | NB4, | Makishima |
| 29 | 9-cis retinoic acid | | | [b] | HT93 | et al, 1996, 1998 |
| 30 | $HOPO_2O$— | | | [b] | RAS | Munteanu |
| 31 | Toc-$OPO_2O$— | | | [b] | MC, THP-1 | et al, 2004 |
| 32 | $^{-}O_2CCH_2CH_2COO$— | 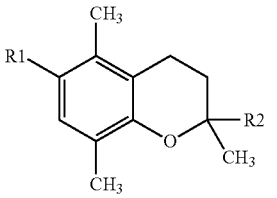 | | 50% of α-TOS | Jurkat, HBT1, MCF7, MCF7-C3, U937, Meso-2 | Birringer et al, 2003; Tomic-Vatic et al, 2005 |
| 33 | $^{-}O_2CCH_2CH_2COO$— | 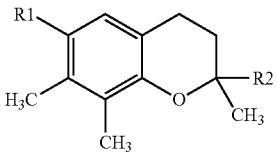 | | [a] | Jurkat, HBT1, MCF7, MCF7-C3 | Birringer et al, 2003; Vraka et al, 2006 |
| 34 | $^{-}O_2CCH_2CH(SePh)COO$— | | | [b] | prostate | Vraka et al, 2006 |

TABLE II-continued

Anti-proliferative activity of vitamin E analogues.
Compounds are sorted by the Signaling Domain.

| Nr | Functional Domain I (R1) | Signalling Domain II | Hydrophobic Domain III (R2) | $IC_{50}$ [μM] | Cell type | Ref (see the list of refs) |
|---|---|---|---|---|---|---|
| 35 | $^{-}O_2CCH_2CH_2COO$— | 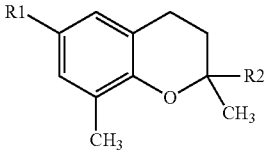 | | 66 | Jurkat, HBT1, MCF7, MCF7-C3 | Birringer et al, 2003; Tomic-Vatic et al, 2005 |
| 36 | $^{-}O_2CCH{=}CHCOO$— | | | 49 | Jurkat, | Tomic- |
| 37 | $^{-}O_2CCH_2CH_2CONH$— | | | 20 | U937, | Vatic et |
| 38 | $^{-}O_2CCH{=}CHCONH$— | | | 9 | Meso-2 | al, 2005 |
| 39 | $H_3COOCCH_2CH_2COO$— | | | [a] | | Birringer et al, 2003 |
| 40 | HO— | | | [b] | PC-3 | Galli et al, 2004 |

[a]No effect;
[b]inhibition of cell proliferation;
[c]much more cytotoxic than α-TOS;
[d]less effective than 54;
[e]ther analogue is less effective than α-TOS itself;
[f](comparable to α-TOS;
[g]EC50[μg/ml];
[h]more efficient than α-TOS.

TABLE III

Anti-proliferative activity of vitamin E analogues with a modified Hydrophobic Domain.

| Nr. | Functional Domain I (R1) | Signalling Domain II | Hydrophobic Domain III (R2) | $IC_{50}$ [μM] | Cell type | Ref |
|---|---|---|---|---|---|---|
| 41 | $^{-}O_2CCH_2CH_2COO$— | 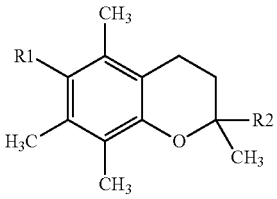 | $COO^{-}$ | [a] | Jurkat, HBT11, MCF7, MCF7-C3 | Birringer et al, 2003 |
| 42 | HO— | | 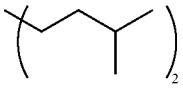 | [a] | LNCaP, | Shiau et |
| 43 | $^{-}O_2CCH_2CH_2COO$— | | | 4-9 | PC-3 | al, 2006 |
| 44 | $^{-}O_2CCH_2CH_2O$— | | | 4-8 | | |
| 45 | $^{-}O_2CCH_2CH_2COO$— | | 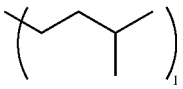 | 8-19 | | |
| 46 | | | $CH_3$ | >100 | | |
| 47 | $^{+}NH_3Lys(NH_3)COO$— | | $CH_2$—OH | 194 | MCF7 | Arya e tal, 1995 |
| 48 | | | $CH_2$—O-$nC_5H_{11}$ | 22 | | |
| 49 | | | $CH_2$—OC(O)$nC_4H_9$ | 15 | | |
| 50 | | | $CH_2$—O-cholic acid | 4 | | |
| 51 | HO— | | $CH_2CH_2COO^{-}$ | [b] | PC-3 | Galli et al, 2004 |
| 52 | HO— | 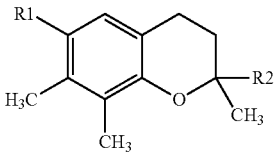 | $CH_2CH_2COO^{-}$ | [c] | | |

[a]No effect;
[b]weak inhibition at 50 μM;
[c]82% inhibition at 10 μM.

TABLE IV

Anti-proliferative activity of vitamin E analogues. Compounds are sorted by the Signaling Domain.

| Nr. | Functional Domain I (R1) | Signalling Domain II | Hydrophobic Domain III (R2) | $IC_{50}$ [μM] | Cell type | Ref. |
|---|---|---|---|---|---|---|
| 53 | HO— | 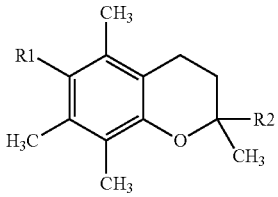 | 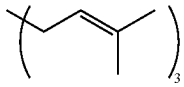 | 210<br>14<br>110 | MDA-MB-435<br>MCF7<br>B16(F10) | Guthrie et al, 1997<br>He et al, 1997 |
| 54 | $CH_3CH_2COO$— | | | [a] | A549 | Yano et al, 2005 |
| 55 | HO— | | 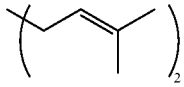 | [b] | Jurkat, HBT11, MCF7, MCF7-C3 | Birringer et al, 2003 |
| 56 | HO— | 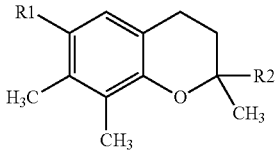 | 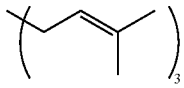 | 4<br>15[c]<br>[d]<br>20 | neoplast Ic + SA mammary epithelial cells<br>MCF7<br>Jurkat, HBT11, MCF7, MCF7-C3<br>B16(F10) | Shah and Sylvester, 2005<br>He et al, 1997<br>Birringer et al, 2003<br>He et al, 1997 |
| 57 | $^{-}O_2CCH_2CH_2COO$— | | | [e]<br>[f] | Jurkat, HBT11, MCF7, MCF7-C3<br>prostate | Birringer et al, 2003<br>Vraka et al, 2006 |
| 58 | $^{-}O_2CCH_2CH(SePh)COO$— | | | [f] | prostate | Vraka et al, 2006 |
| 59 | HO— | 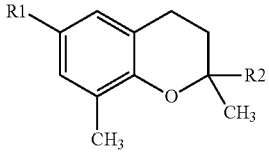 | | 10<br>[b]<br>15[c] | B16(F10)<br>MDA-MB-435, MCF7<br>MCF7 | He et al, 1997<br>Shun et al, 2004<br>Nesaretnam et al, 1998 |
| 60 | HO— | 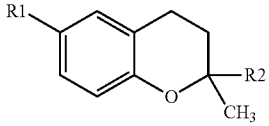 | | 0.9 | B16(F10) | He et al, 1997 |

[a]Cytotoxic in 0-40 μM range;
[b]very potent;
[c]complete inhibition;
[d]comparable to α-TOS;
[e]2-fold more potent than γ-tocotrienol;
[f]inhibition of cell proliferation.

The second domain, termed the Signaling Domain (II), exhibits some activities that are independent of the anti-oxidant properties of the tocopherols. These properties derive from the methylation pattern of the aromatic ring. For example, α-tocopherol has been reported to inhibit protein kinase C (PKC) by decreasing diacylglycerol (DAG) levels, while other tocopherols with similar anti-oxidant capabilities (e.g., β-tocopherol) do not inhibit PKC. Thus, the PKC inhibitory activity of α-tocopherol is independent of its anti-oxidant capacity (Tasinato A, Boscoboinik D, Bartoli G M, Maroni P and Azzi A (1995) d-α-Tocopherol inhibition of vascular smooth muscle cell proliferation occurs at physiological concentrations, correlates with protein kinase C inhibition, and is independent of its antioxidant properties. Proc Natl Acad Sci USA 92:12190-12194; Kunisaki M, Bursell S E, Clermont A C, Ishii H, Ballas L M, Jirousek M R, Umeda F, Nawata H and King G L (1995) Vitamin E prevents diabetes-induced abnormal retinal blood flow via the diacylglycerol-protein kinase C pathway. Am J Physiol 269:E239-246). In some cases, however, the biological activity of the various tocopherols is influenced by structural differences in the Signaling Domain, which do indeed have a profound impact on their anti-oxidant activity against certain species. γ-Tocopherol, for example, is a much better scavenger of reactive nitrogen oxide species (e.g., peroxynitrite) than α-tocopherol. Hence, the γ-molecule, which lacks a methyl group at C5, is readily nitrated at that site (Morton L W, Ward N C, Croft K D, Puddey I B. (2002) Evidence for the nitration of gamma-tocopherol in vivo: 5-nitro-gamma-tocopherol is elevated in the plasma of subjects with coronary heart disease. Biochem J. June 15; 364(Pt 3):625-8; Christen S, Woodall A A, Shigenaga M K, Southwell-Keely P T, Duncan M W, Ames B N. (1997) gamma-tocopherol traps mutagenic electrophiles such as NO(X) and complements alpha-tocopherol: physiological implications. Proc Natl Acad Sci USA. April 1; 94(7):3217-22).

The lipophilic side chain of vitamin E isomers distinguishes between tocopherols with saturated isoprenyl units and tocotrienols with unsaturated isoprenyl units. The Hydrophobic Domain (III) determines whether the molecule can bind to lipoproteins and membranes respectively, or be degraded by phase I enzymes (Birringer M, Pfluger P, Kluth D, Landes N and Brigelius-Flohe R (2002) Identities and differences in the metabolism of tocotrienols and tocopherols in HepG2 cells. J Nutr 132:3113-3118; Neuzil J, Massa H (2005) Hepatic processing determines dual activity of vitamin E succinate. Biochem Biophys Res Commun 327: 1024-1027).

Many tocopherol derivatives with a modified hydroxyl group have been tested for their pro-apoptotic activity (Table II). The most prominent derivative tested has been α-TOS (entry 1) bearing a succinylester at position C6 of the chromanol ring. Due to its low $pK_{\alpha}$ (<6), α-TOS is fully deprotonated under physiological conditions, leading to a detergent-like molecule which destabilizes mitochondrial membranes and has an effect on complex II. Dicarboxylic esters of tocopherols present the best studied compounds for structure-activity relationship (SAR). Strong apoptogens included α-tocopherol succinate (1), oxalate (10), and malonate (11), the latter two inducing non-selective cytotoxicity in mice inoculated with B16-F1 melanoma cells (Kogure K, Manabe S, Suzuki I, Tokumura A and Fukuzawa K (2005) Cytotoxicity of α-tocopheryl succinate, malonate and oxalate in normal and cancer cells in vitro and their anti-cancer effects on mouse melanoma in vivo. J Nutr Sci Vitaminol 51:392-397). Even greater pro-apoptotic activity has been observed for unsaturated dicarboxylic acids like α-tocopheryl maleate (3) (Birringer M, EyTina J H, Salvatore B A and Neuzil J (2003) Vitamin E analogues as inducers of apoptosis: Structure-function relationship. Br J Cancer 88:1948-1955) and α-tocopheryl fumarate. Increasing the chain length of the dicarboxylic acid led to decreased activity as shown for glutaric acid (5), methylated glutaric acids (6, 7, 8) (Birringer et al, 2003) with the pimelic acid (24) (Kogure K, Hama S, Kisaki M, Takemasa H, Tokumura A, Suzuki I and Fukuzawa K (2004) Structural characteristic of terminal dicarboxylic moiety required for apoptogenic activity of α-tocopheryl esters. Biochim Biophys Acta 1672: 93-99) exhibiting no activity at all.

It has been established that the whole α-TOS molecule is necessary for its full apoptosis inducing activity (Birringer M, EyTina J H, Salvatore B A and Neuzil J (2003) Vitamin E analogues as inducers of apoptosis: Structure-function relationship. Br J Cancer 88:1948-1955). Esterification of the free carboxyl group leads to non-charged derivatives without pro-apoptotic activity (9, 25). Aliphatic carboxylic acid esters, such as tocopheryl acetate and propionate (19), respectively, were inactive as was the methyl ether (18). Oral administration of α-TOS is not effective since the compound is cleaved by intestinal esterases (Wu Y, Zu K, Ni J, Yeh S, Kasi D, James N S, Chemler S and Ip C (2004) Cellular and molecular effects of α-tocopheryloxybutyrate: lessons for the design of vitamin E analog for cancer prevention. Anticancer Res 24:3795-3802; Cheeseman K H, Holley A E, Kelly F J, Wasil M, Hughes L and Burton G (1995) Biokinetics in humans of RRR-α-tocopherol: the free phenol, acetate ester, and succinate ester forms of vitamin E. Free Radic Biol Med 19:591-598). To overcome the problem of ester bond cleavage, compounds (20, 21) and a side chain-truncated derivative (42) have been synthesized, replacing the ester bond with an ether bond, since the latter is resistant to hydrolysis (Wu Y, Zu K, Ni J, Yeh S, Kasi D, James N S, Chemler S and Ip C (2004) Cellular and molecular effects of α-tocopheryloxybutyrate: lessons for the design of vitamin E analog for cancer prevention. Anticancer Res 24:3795-3802; Nishikawa K, Satoh H, Hirai A, Suzuzki K, Asano R, Kumadaki I, Hagiwara K and Yano T (2003) α-Tocopheryloxybutyric acid enhances necrotic cell death in breast cancer cells treated with chemotherapy agent. Cancer Lett 201:51-56; Shun M C, Yu W, Gapor A, Parsons R, Atkinson J, Sanders B G and Kline K (2004) Pro-apoptotic mechanisms of action of a novel vitamin E analog (α-TEA) and a naturally occurring form of vitamin E (δ-tocotrienol) in MDA-MB-435 human breast cancer cells. Nutr Cancer 48:95-105; Shiau C W, Huang J W, Wang D S, Weng J R, Yang C C, Lin C H, Li C, Chen C S (2006) alpha-Tocopheryl succinate induces apoptosis in prostate cancer cells in part through inhibition of Bcl-xL/Bcl-2 function. J Biol Chem 281:11819-11825). It should be noted that the replacement of the ether bond by a methylene group is sufficient to accelerate apoptosis (22) (Sanders G., et al (2001) Preparation of tocopherols, tocotrienols, other chroman and side chain derivatives that induce cell apoptosis for therapeutic use as antiproliferative agents. 2001: PCT Int. Appl. WO 2001058889. p. 120).

When the ester bond is replaced by an amide bond, further enhancement of pro-apoptotic activity was observed (12, 13, 37, 38) (Tomic-Vatic A, EyTina J H, Chapmann J M, Mandavian E, Neuzil J and Salvatore B A (2005) Vitamin E amides, a new class of vitamin E analogues with enhanced pro-apoptotic activity. Int J Cancer 117:118-193). Again the unsaturated amides (13, 38) were superior to the saturated amides. The rationale for introducing an amide bond in place of the ester was based on the well-established fact that anilinic amides are much less prone to hydrolysis than the corresponding phenolic esters. Enhancing the stability of these tocopheryl ester derivatives would protect these molecules in vivo, allowing them to stay intact longer, thereby increasing their bioavailability. The isosteric replacement of the esters by amides makes that linkage less prone to enzymatic hydrolysis as well. Several nonspecific esterases exist in the intestinal mucosal cells and in the blood. In contrast, peptidases exhibit a much narrower specificity. For example, pro-drugs with an amino acid in an amide linkage are more stable in the intestine and blood than their corresponding ester analogues (Sugawara M, Huang W, Fei Y-J, Leibach F H, Ganaphthy V and Ganaphthy M E (2000) Transport of valganciclovir, a ganciclovir prodrug, via peptide transporters PEPT1 and PEPT2. J Pharm Sci 89:781-789).

The last group of compounds consisted of a series of lysine α-tocopheryl esters with a positively charged N-terminus (15-17). The hydrophilic ammonium functionality exerted similar pro-apoptotic effects to its carboxylate counterpart, suggesting a general motif is required for activity that consists of a lipophilic side chain and a hydrophilic head group. However, succinyl esters of long chain aliphatic alcohols (e.g., phytol and oleol) did not show any activity (Birringer M, EyTina J H, Salvatore B A and Neuzil J (2003)

Vitamin E analogues as inducers of apoptosis: Structure-function relationship. Br J Cancer 88:1948-1955).

A general SAR can be drawn from the data shown in Table II:

1. To gain profound pro-oxidant and pro-apoptotic activity, modifications of the Functional Domain I required a hydrophilic head group consisting of a dissociated acid or a charged ammonium group.
2. The chain length and the degree of unsaturation of the Functional Domain determined the apoptogenic activity. Conformational restrictions appeared to potentiate the activity.
3. The chemical linkage of the Functional Domain is not limited to esters, and other functionalities prevented enzymatic degradation of the derivatives.

The substitution pattern of the chromanol ring is often not merely related to the anti-oxidant properties of the tocopherols (Azzi A, Ricciarelli R and Zingg J M (2002) Non-antioxidant molecular functions of α-tocopherol (vitamin E). FEBS Lett 519:8-10). Different biochemical observations emphasize the role of α-tocopherol in signaling and metabolic processes. Thus, α-tocopherol is selectively recognized in the liver by α-tocopherol transfer protein (α-TTP), a 32 kDa protein with a high affinity for α-tocopherol relative to the other tocopherols and tocotrienols. The relative affinities for α-TTP decrease with the loss of methylation of the chromanol ring α-tocopherol 100%, β-tocopherol 38%, γ-tocopherol 9% and δ-tocopherol 2%) (Hosomi A, Arita M, Sato Y, Kiyose C, Ueda T, Igarashi 0, Arai H and Inoue K (1997) Affinity for α-tocopherol transfer protein as a determinant of the biological activities of vitamin E analogs. FEBS Lett 409:105-108). The recently discovered tocopherol associated proteins (TAPS) show similar preferences in tocopherol binding (Yamauchi J, Iwamoto T, Kida S, Masushige S, Yamada K and Esashi T (2001) Tocopherol-associated protein is a ligand-dependent transcriptional activator. Biochem Biophys Res Commun 285:295-299). In endothelial cells, thrombin-induced PKC activation and endothelin secretion are inhibited by α-tocopherol but not by β-tocopherol (Martin-Nizard F, Boullier A, Fruchart, J C and Duriez P (1998) α-Tocopherol but not β-tocopherol inhibits thrombin-induced PKC activation and endothelin secretion in endothelial cells. J Cardiovasc Risk 5:339-345). At the transcriptional level α-tocopherol causes up-regulation of α-tropomyosin expression (Aratri E, Spycher S E, Breyer I and Azzi A (1999) Modulation of α-tropomyosin expression by α-tocopherol in rat vascular smooth muscle cells. FEBS Lett 447:91-94) and down regulation of LDL scavenger receptors SR-A and CD36, whereas β-tocopherol is ineffective (Ricciarelli R, Zingg J M and Azzi A (2000) Vitamin E reduces the uptake of oxidized LDL by inhibiting CD36 scavenger receptor expression in cultured aortic smooth muscle cells. Circulation 102:82-87; Devaraj S, Hugou I and Jialal I (2001) α-Tocopherol decreases CD36 expression in human monocyte-derived macrophages. J Lipid Res 42:521-527). In addition, the substitution pattern is likely responsible for the rate of side chain degradation because in cell culture, γ- and δ-tocopherol are degraded much faster than α- or β-tocopherol (Birringer M, Drogan D and Brigelius-Flohe R (2001) Tocopherols are metabolized in HepG2 cells by side chain ω-oxidation and consecutive β-oxidation. Free Radic Biol Med 31:226-232). Succinylation of the four tocopherol isomers produces the compounds 1, 32, 33 and 35. It is not surprising that of these, α-TOS (1) possesses the highest apoptogenic activity tested, followed by β-TOS (32), γ-TOS (33) and δ-TOS (35) as the least effective (Birringer M, Drogan D and Brigelius-Flohe R (2001) Tocopherols are metabolized in HepG2 cells by side chain ω-oxidation and consecutive β-oxidation: Free Radic Biol Med 31:226-232). In general, the more highly methylated members of the tocopherol family are the most potent, but this trend is reversed for the tocotrienols (see below).

Succinylation of Trolox, a water soluble vitamin E derivative with a shortened side chain, resulted in the complete loss of pro-apoptotic activity. SAR experiments of various tocopherol succinates bearing truncated phytol side chains (Table III, 43, 44, 45) revealed the highest level of apoptogenic activity in prostate cancer cells was obtained with derivatives where the side chain length was two isoprenyl units (43, 44). Computer assisted molecular modeling and co-immunoprecipitation experiments showed that the binding of Bak BH3 peptide to Bcl-$x_L$ and Bcl-2 was inhibited by the tocopherol analogues (Shiau C W, Huang J W, Wang D S, Weng J R, Yang C C, Lin C H, Li C, Chen C S (2006) alpha-Tocopheryl succinate induces apoptosis in prostate cancer cells in part through inhibition of Bcl-xL/Bcl-2 function. J Biol Chem 281:11819-11825). Central requirements for anti-neoplastic activity were succinylation of the chromanol ring and a minimum chain length of one isoprenyl unit (42, 46). A series of tocopheryl lysine esters with ether/ester linked Domain III side chains also showed a negative correlation between chain length and $IC_{50}$ (47-50) (Arya P, Alibhai N, Qin H, Burton G W, Batist G, You S X and Alaoui-Jamali M A (1998) Design and synthesis of analogues of vitamin E: antiproliferative activity against human breast adenocarcinoma cells. Bioorg Med Chem Lett 8:2433-2438).

Tocotrienols are efficient anti-cancer agents and their pro-apoptotic property may be related to the inactivation of the Ras family of proteins. Tocotrienols exhibit their pro-apoptotic activity without modifications of the Functional Domain. The hierarchy in the Signaling Domain is also reversed, making δ-tocotrienol (59) the most potent agent in the murine B16-F10 melanoma cell model, followed by γ-(56) and α-tocotrienol (53) (Table IV; He L, Mo H, Hadisusilo S, Qureshi A A and Elson C E (1997) Isoprenoids suppress the growth of murine B16 melanomas in vitro and in vivo. J Nutr 127:668-674). Interestingly, desmethyl tocotrienol (60), lacking all aromatic methyl groups, shows even higher activity with an $IC_{50}$ of 0.9 μM. This compound has been isolated from rice bran (Qureshi A A, Mo H, Packer L and Peterson D M (2000) Isolation and identification of novel tocotrienols from rice bran with hypocholesterolemic, anti-oxidant, and antitumor properties. J Agric Food Chem 48:3130-3140). A direct inhibitory action of tocotrienols has been proposed because the membrane anchoring cysteine residue of Ras proteins is modified by a common structural element, a farnesyl chain. Thus, Ras farnesylation and RhoA prenylation was inhibited by tocotrienols in A549 cells, a human lung adenocarcinoma cell line containing an activating ras mutation (Yano Y, Satoh H, Fukumoto K, Kumadaki I, Ichikawa T, Yamada K, Hagiwara K and Yano T (2005) Induction of cytotoxicity in human lung adenocarcinoma cells by 6-O-carboxy-propyl-α-tocotrienol, a redox-silent derivative of α-tocotrienol. Int J Cancer 115:839-846). To expand the short in vivo half life of tocotrienols, functional domains have been introduced. These modifications also enhanced the anti-proliferative activity of the molecules (54, 57, 58). Truncation of the side chain also improved activity, similar to that found for compound 55.

A number of compounds where modifications have been made to the Functional Domain exhibit anti-proliferative activity and provide additional specialized properties. For example, α-Tocopheryl polyethylene glycol succinate (23)

has been used as a vehicle for drug delivery systems. This compound was shown to possess anti-cancer activity against human lung carcinoma cells implanted in nude mice. The apoptosis inducing efficacy of the compound was not due to its increased uptake into cells, but rather due to an increased ability to generate reactive oxygen species (Youk H J, Lee E, Choi M K, Lee Y J, Chung J H, Kim S H, Lee C H and Lim S J (2005) Enhanced anticancer efficacy of α-tocopheryl succinate by conjugation with polyethylene glycol. J Control Release 107:43-52). α-Tocopheryl phosphate (30) is believed to result from metabolism occurring during tocopherol-associated signaling (Negis Y, Zingg J M, Ogru E, Gianello R, Libinaki R and Azzi A (2005) On the existence of cellular tocopheryl phosphate, its synthesis, degradation and cellular roles: a hypothesis. IUBMB Life 57:23-25). Mixtures of 30 and di-α-tocopheryl phosphate (31) inhibited proliferation in rat aortic smooth muscle cells and in human THP-1 monocytic leukaemia cells (Munteanu A, Zingg J M, Ogru E, Libinaki R, Gianello R, West S, Negis Y and Azzi (2004) Modulation of cell proliferation and gene expression by α-tocopheryl phosphates: relevance to atherosclerosis and inflammation. Biochem Biophys Res Commun 318:311-316). The authors proposed that tocopheryl succinate and tocopheryl maleate may act in cancer cells by mimicking and substituting for tocopheryl phosphate and thereby cause the permanent activation of cellular signals.

Two experimental α-tocopheryl esters of all-trans retinoic acid (28) and 9-cis retinoic acid (29), respectively, have been used to reduce proliferation of acute promyelocytic leukaemia cells (Makishima M, Umesono K, Shudo K, Naoe T, Kishi K and Honma Y (1998) Induction of differentiation in acute promyelocytic leukemia cells by 9-cis retinoic acid α-tocopherol ester (9-cis tretinoin tocoferil). Blood 91:4715-4726). Trans-activation experiments with retinoid receptor responsive reporter constructs revealed that both of these compounds acted as agonists for retinoic acid receptors (RARs). γ-Carboxyethyl hydroxychroman (52), a degradation product of γ-tocopherol often found secreted in the urine, is able to reduce cell proliferation of PC-3 prostate cancer cells by inhibiting cyclin D1 expression (Galli F, Stabile A M, Betti M, Conte C, Pistilli A, Rende M, Floridi A and Azzi A (2004) The effect of α- and γ-tocopherol and their carboxyethyl hydroxychroman metabolites on prostate cancer cell proliferation. Arch Biochem Biophys 423:97-102).

A commonly observable difference in cancer cell compared to normal cell mitochondria is the greater mitochondrial inner trans-membrane potential (ΔΨm,i) in cancer cells. For example, as a result of the metabolic changes occurring inside cancer cells and their mitochondria, the ΔΨm,i is increased to greater negative values (−150 to −170 mV, negative inside the matrix) in carcinoma cells (Summerhayes, I. C., Lampidis, T. J., Bernal, S. D., Nadakavukaren, J. J., Nadakavukaren, K. K., Shepherd, E. L. and Chen, L. B. (1982) Unusual retention of rhodamine 123 by mitochondria in muscle and carcinoma cells. Proc Natl Acad Sci USA 79:5292-5296; Lampidis, T. J., Bernal, S. D., Summerhayes, I. C. and Chen, L. B. 1983. Selective toxicity of rhodamine 123 in carcinoma cells in vitro. Cancer Res. 43:716-720; Chen, L. B. 1988. Mitochondrial membrane potential in living cells. Annu Rev Cell Biol. 4:155-181; Modica-Napolitano, J. S. and Aprille, J. R. 1987. Basis for the selective cytotoxicity of rhodamine 123. Cancer Res. 47:4361-4365; Modica-Napolitano, J. S. and Aprille, J. R. 2001. Delocalized lipophilic cations selectively target the mitochondria of carcinoma cells. Adv Drug Deliv Rev. 49:63-70), with ~60 mV difference across the MIM. Many proposals have been made to explain the reasons for this difference in membrane potential. At the molecular level, these include differences in mitochondrial respiratory enzyme complexes, electron carriers, ATPase, ANT and/or changes in membrane lipid metabolism. Other proposals for the increased mitochondrial membrane potential in cancer cells include altered electron transfer activity, proton translocation and utilization, or conductance. For example, mitochondria isolated from hepatocellular carcinomas display reduced uncoupler-stimulated ATP hydrolysis, decreased rates of respiration-linked ATP synthesis and reduced phosphorylating capacity compared with normal liver cells [Pedersen, P. L. and Morris, H. P. 1974. Uncoupler stimulated adenosine triphosphatase activity. Deficiency in intact mitochondria from Morris hepatomas and ascites tumor cells. J Biol. Chem. 249:3327-3334; Capuano, F., Varone, D., D'Eri, N., Russo, E., Tommasi, S., Montemurro, S., Prete, F. and Papa, S. 1996. Oxidative phosphorylation and $F_0F_1$ ATP synthase activity of human hepatocellular carcinoma. Biochem Mol Biol Int. 38:1013-1022; Capuano, F., Guerrieri, F. and Papa, S. 1997. Oxidative phosphorylation enzymes in normal and neoplastic cell growth. J Bioenerg Biomembr. 29:379-384; Cuezva, J. M., Ostronoff, L. K., Ricart, J., Lopez de Heredia, M., Di Ligero, C. M. and Izquierdo, J. M. 1997. Mitochondrial biogenesis in the liver during development and oncogenesis. J Bioenerg Biomembr. 29:365-377].

Marked changes in enzyme function, particularly in the ATPase, have been shown to occur in cancer cell mitochondria. Thus, preparations of ATPase isolated from carcinomas show reduced maximal velocity, decreased immunodetectable levels of the β subunit of the F1 component of mitochondrial ATPase and/or overexpression of the ATPase inhibitor protein (IF1) Pedersen, P. L. and Morris, H. P. 1974. Uncoupler stimulated adenosine triphosphatase activity. Deficiency in intact mitochondria from Morris hepatomas and ascites tumor cells. J. Biol. Chem. 249:3327-3334; Capuano, F., Varone, D., D'Eri, N., Russo, E., Tommasi, S., Montemurro, S., Prete, F. and Papa, S. 1996. Oxidative phosphorylation and $F_0F_1$ ATP synthase activity of human hepatocellular carcinoma. Biochem Mol Biol Int. 38:1013-1022; Capuano, F., Guerrieri, F. and Papa, S. 1997. Oxidative phosphorylation enzymes in normal and neoplastic cell growth. J Bioenerg Biomembr. 29:379-384; Cuezva, J. M., Ostronoff, L. K., Ricart, J., Lopez de Heredia, M., Di Ligero, C. M. and Izquierdo, J. M. 1997. Mitochondrial biogenesis in the liver during development and oncogenesis. J Bioenerg Biomembr, 29:365-377; reviewed in Modica-Napolitano, J. S. and Singh, K. 2002. Mitochondria as targets for detection and treatment of cancer. Expert Rev Mol. Med. 2002:1-19). A reduced ability to use the proton gradient to make ATP, with a resulting build up in the protons within the MIM would account for the greater ΔΨm,i existing in tumour mitochondria. Another possibility that may account for greater ΔΨm,i in cancer cells is that acetoin undergoes an ATP dependent reaction, almost doubling the reaction rate to produce citrate in tumour cells (Baggetto, L. G. and Lehninger, A. L. 1987. Isolated tumoral pyruvate dehydrogenase can synthesize acetoin which inhibits pyruvate oxidation as well as other aldehydes. Biochem Biophys Res Commun. 145:153-159; Baggetto, L. G. and Testa-Parussini, R. 1990. Role of acetoin on the regulation of intermediate metabolism of Ehrlich ascites tumor mitochondria: its contribution to membrane cholesterol enrichment modifying passive proton permeability. Arch Biochem Biophys. 283:241-248), which is then exported by the tricarboxylate or citrate carrier (CIC) to the cytosol where it is cleaved to oxaloacetate and acetyl-coA. The net effect is the provision of a high level of cytoplasmic acetyl-coA precursor for sterol biosynthesis, particularly helping to promote the already elevated cancer cell production of cholesterol (Baggetto, L. G. and Testa-Parussini, R. 1990. Role of acetoin on the regulation of intermediate metabolism of Ehrlich ascites tumor mitochondria: its contribution to membrane cholesterol enrichment modifying passive proton permeability. Arch Biochem Biophys. 283:241-248). The resulting build-up of cholesterol in the inner MIM reduces several fold their passive proton permeability, helping to establish the greater transmembrane potential in cancer cells (Baggetto, L. G. and Testa-Parussini, R. 1990. Role of acetoin on the regulation of intermediate metabolism of Ehrlich ascites tumor mitochondria: its contribution to membrane cholesterol enrichment modifying passive proton permeability. Arch Biochem Biophys. 283:241-248; Baggetto, L. G. 1992. Deviant energetic metabolism of glycolytic cancer cells. Biochimie. 74:959-974).

The enhanced glycolytic activity due to very high energetic demand increases cytoplasmic levels of lactic acid production in cancer cells. To maintain the neutral pH of the cytosol these cells activate plasma membrane proton pumps causing extracellular acidification. Typically, the pH of the tumour interstitium is 6.2-6.5, while the pH of normal tissue interstitium is neutral (Gerweck, L. E. 2000. The pH difference between tumor and normal tissue offers a tumor specific target for the treatment of cancer. Drug Resist Updat. 3:49-50; Gerweck, L. E., Vijayappa, S. and Kozin, S. 2006. Tumor pH controls the in vivo efficacy of weak acid and base chemotherapeutics. Mol Cancer Ther. 5:1275-1279). The major type of proton pumps used by cancer cells to maintain their neutral cytosolic pH is the class V ATPase (Sennoune, S. R., Luo, D. and Martinez-Zaguilan, R. 2004. Plasmalemmal vacuolar-type H+-ATPase in cancer biology. Cell Biochem Biophys. 40:185-206). This ATPase has relatively low activity in non-malignant cells, while its activity is increased in cancer cells (Izumi, H., Torigoe, T., Ishiguchi, H., Uramoto, H., Yoshida, Y, Tanabe, M., Ise, T., Murakami, T., Yoshida, T., Nomoto, M. and Kohno, K. 2003. Cellular pH regulators: potentially promising molecular targets for cancer chemotherapy. Cancer Treat Rev. 29:541-549; Bowman, E. J. and Bowman, B. J. 2005. V-ATPases as drug targets. J Bioenerg Biomembr. 37:431-435). These observations led to development of a novel anti-cancer strategy by inhibiting the proton pumping activity of the ATPase, causing acidification of the cancer cell cytosol that, in turn, results in the demise of the cell. For example, chondropsin compounds (Bowman, E. J., Gustafson, K. R., Bowman, B. J. and Boyd, M. R. 2003. Identification of a new chondropsin class of antitumor compound that selectively inhibits V-ATPases. J Biol. Chem. 278: 44147-44152) and siRNA targeting the ATPase subunit ATP6L (Lu, X., Qin, W., Li, J., Tan, N., Pan; D., Zhang, H., Xie, L., Yao, G., Shu, H., Yao, M., Wan, D., Gu, J. and Yang, S. (2005) The growth and metastasis of human hepatocellular carcinoma xenografts are inhibited by small interfering RNA targeting to the subunit ATP6L of proton pump. Cancer Res. 65:6843-6849) have been successfully used to kill cancer cells. Other important regulators of cytosolic pH are the Na+/H+ antiporter (Slepkov, E. R., Rainey, J. K., Sykes, B. D. and Fliegel, L. 2007. Structural and functional analysis of the Na+/H+ exchanger. Biochem J. 401:623-633), the H+/lactate symporter (Cardone, R. A., Casavola, V. and Reshkin, S. J. 2005. The role of disturbed pH dynamics and the Na+/H+ exchanger in metastasis. Nat Rev Cancer. 5:786-795), and the Na+-dependent Cl–/HCO-exchanger (Lee, A. H. and Tannock, I. F. 1998. Heterogeneity of intracellular pH and of mechanisms that regulate intracellular pH in populations of cultured cells. Cancer Res. 58:1901-1908). Similarly as for V-class ATPase, these transporters have been proposed as targets for anticancer drugs (Izumi, H., Torigoe, T., Ishiguchi, H., Uramoto, H., Yoshida, Y., Tanabe, M., Ise, T., Murakami, T., Yoshida, T., Nomoto, M. and Kohno, K. 2003. Cellular pH regulators: potentially promising molecular targets for cancer chemotherapy. Cancer Treat Rev. 29:541-549 Cardone, R. A., Casavola, V. and Reshkin, S J 2005. The role of disturbed pH dynamics and the Na+/H+ exchanger in metastasis. Nat Rev Cancer. 5:786-795; Harguindey, S., Orive, G., Luis Pedraz, J., Paradiso, A. and Reshkin, S. J. 2005. The role of pH dynamics and the Na+/H+ antiporter in the etiopathogenesis and treatment of cancer. Two faces of the same coin—one single nature. Biochim Biophys Acta. 1756:1-24).

The difference in pH gradient across the plasma membrane of cancer cells has been used to design a class of drugs that can be classified as weak acids, with pKa values of <6, and which are, typically, deprotonated at neutral pH but accept a proton at the pH of the tumour interstitium (Gerweck, L. E., Vijayappa, S. and Kozin, S. 2006. Tumor pH controls the in vivo efficacy of weak acid and base chemotherapeutics. Mol Cancer Ther. 5:1275-1279). A prototypic example of such a drug is the weak acid chlorambucil (Skarsgard, L. D., Chaplin, D J., Wilson, D. J., Skwarchuk, M. W., Vinczan, A. and Kristl, J. 1992. The effect of hypoxia and low pH on the cytotoxicity of chlorambucil. Int J Radiat Oncol Biol Phys. 22:737-741). It was reported that the relatively selective uptake and anti-cancer efficacy of chlorambucil could be enhanced by injection of glucose into mice with experimental tumours, thereby further promoting glycolytic activity of tumour cells, lowering the tumour interstitium pH while not affecting the pH of the tumour cell cytosol (Kozin, S. V., Shkarin, P. and Gerweck, L. E. (2001) The cell transmembrane pH gradient in tumors enhances cytotoxicity of specific weak acid chemotherapeutics. Cancer Res. 61:4740-4743).

The present inventors have observed similar effects for the mitocan α-tocopheryl succinate (α TOS), a compound with pKa of 5.6 (Neuzil, J., Zhao, M., Ostermann, G., Sticha, M., Gellert, N., Weber, C., Eaton, J. W. and Brunk, U. T. 2002 α-Tocopheryl succinate, an agent with in vivo anti-tumour activity, induces apoptosis by causing lysosomal instability. Biochem J. 362:709-715). The vitamin E analogue is a weak acid, of which ~98% is deprotonated at neutral pH with 10-15-fold higher percentage in the protonated form at the acidic pH of 6.2-6.4 of the tumour interstitium. Since there are no known transporters for compounds like α-TOS, presumably it crosses the plasma membrane to freely diffuse inside the cells and discharge its apoptogenic activity. Accordingly, the present inventors have found that when the pH of the tissue culture medium was more acidic (pH ~6.2), it resulted in ~3-times greater apoptogenic efficacy of α-TOS against T lymphoma cells compared to media at pH of 7.2. The likely reason is the faster uptake of the compound at lower pH, since it was found that about twice as much α-TOS enters at pH 6.2 than when the pH of the medium was 7.4 (Neuzil, J., Zhao, M., Ostermann, G., Sticha, M., Gellert, N., Weber, C., Eaton, J. W. and Brunk, U. T. 2002 α-Tocopheryl succinate, an agent with in vivo anti-tumour activity, induces apoptosis by causing lysosomal instability. Biochem J. 362: 709-715). Thus, the pH differential across tumour plasma membranes may be an important paradigm for targeted delivery whereby certain anticancer agents exert selectivity for malignant tissues.

The sixth class of mitocans listed in Table I includes molecules that are delocalized lipophilic cations which accumulate at much greater concentrations in the mitochondrial matrix than in the cytoplasm of cells (Smith, R. A., Porteous, C. M., Gane, A. M. and Murphy, M. P. 2003. Delivery of bioactive molecules to mitochondria in vivo. Proc Natl Acad Sci USA 100:5407-5412). These agents are selectively accumulated in the mitochondrial matrix of cancer cells because of their greater transmembrane potentials across the plasma membrane as well as their more polarized mitochondria with a much greater $\Delta\Psi m,i$ than that in non-malignant cells (Davis, S., Weiss, M. J., Wong, J. R., Lampidis, T. J. and Chen, L. B. 1985. Mitochondrial and plasma membrane potentials cause unusual accumulation and retention of rhodamine 123 by human breast adenocarcinoma-derived MCF-7 cells. J Biol. Chem. 260:13844-13850; Lampidis, T. J., Hasin, Y, Weiss, M. J. and Chen, L. B. 1985. Selective killing of carcinoma cells "in vitro" by lipophilic-cationic compounds: a cellular basis. Biomed Pharmacother. 39:220-226; Ralph, S. J., Low, P., Dong, L., Lawen, A. and Neuzil, J. 2006. Mitocans: mitochondrial targeted anticancer drugs as improved therapies and related patent documents. Recent Patents Anti-cancer Drug Discovery 1:327-346).

The target for the lipophilic cation-based mitocans may be one of the inhibitory binding sites on ATPase (Gledhill, J. R. and Walker, J. E. 2005. Inhibition sites in F1-ATPase from bovine heart mitochondria. Biochem J. 386:591-598). One of the earliest members of this class of compounds to be identified for its anti-cancer activity was rhodamine-123 (Bernal, S. D., Lampidis, T. J., Summerhayes, I. C. and Chen, L. B. 1982. Rhodamine-123 selectively reduces clonal growth of carcinoma cells in vitro. Science 218:1117-1119; Bernal, S. D., Lampidis, T. J., Mclsaac, R. M. and Chen, L. B. 1983. Anti-carcinoma activity in vivo of rhodamine 123, a mitochondrial-specific dye. Science 222:169-172). It recently entered phase I clinical trials for prostate cancer and revealed minimal side effects and safe administration at monthly intervals without detectable drug accumulation in the serum of patients (Jones, L. W., Narayan, K. S., Shapiro, C. E. and Sweatman, T. W. 2005. Rhodamine-123: therapy for hormone refractory prostate cancer, a phase I clinical trial. J Chemother. 17:435-440). It is likely that the related compound, Rose Bengal, works in a similar fashion to rhodamine 123, and Rose Bengal is likewise currently in clinical trials as a therapy for metastatic melanoma and recurrent breast cancer, causing complete remissions in some patients (Provectus PV-10-MM-01, www.ClinicalTrials.gov).

The drug F16 is a mechanistically more characterized example of this mitocan class and was shown to increase ROS production, depolarize mitochondria as a weak protonophore and collapse $\Delta\Psi m,i$ leading to mitochondrial permeability transition and selective apoptosis of cancer cells when applied in the micromolar range (Fantin, V. R., Berardi, M. J., Scorrano, L., Korsmeyer, S. J. and Leder, P. (2002) A novel mitochondriotoxic small molecule that selectively inhibits tumor cell growth. Cancer Cell 2:29-42). F16 was also reported in the study to inhibit the growth of mammary tumours in mice. MKT-077, a rhodocyanine dye analogue is another example of this type of mitocan that entered phase I clinical trials, although these were terminated due to renal toxicity (Britten, C. D., Rowinsky, E. K., Baker, S. D., Weiss, G. R., Smith, L., Stephenson, J., Rothenberg, M., Smetzer, L., Cramer, J., Collins, W., Von Hoff, D. D. and Eckhardt, S. G. 2000. A phase I and pharmacokinetic study of the mitochondrial-specific rhodacyanine dye analog MKT 077. Clin Cancer Res. 6:42-49).

This raises the issue of toxicity with many of the class VI mitocans. A cautionary example of the potential for toxicity that must be carefully evaluated is the production of Parkinson's-like effects by the drug MPTP (1-methyl-4-phenyl-1,2,3,6-tetrahydropyridine) caused by the selective destruction of the nigrostriatal dopaminergic neurons. This toxicity was due to the selective uptake by the dopamine transporters on these cells as well as metabolites formed by the action of the enzyme, monoamine oxidase B that is highly expressed in the dopaminergic neurons. As a result of these two unique properties of dopaminergic neurons, the mitochondriotoxic drug MPP+ (1-methyl-4-phenylpyridinium) is produced which acts as an inhibitor of mitochondrial respiration by blocking the NADH-ubiquinone oxidoreductase site of complex I. It is likely that MPP+ is also a protonophore (Davey, G. P., Tipton, K. F. and Murphy, M. P. 1992. Uptake and accumulation of 1-methyl-4-phenylpyridinium by rat liver mitochondria measured using an ion-selective electrode. Biochem J. 288:439-443; Albores, R., Neafsey, E J., Drucker, G., Fields, J. Z. and Collins, M. A. 1990. Mitochondrial respiratory inhibition by N-methylated$\beta$-carboline derivatives structurally resembling N-methyl-4-phenylpyridine. Proc Natl Acad Sci USA 87:9368-9372) that collapses the $\Delta\Psi m,i$ leading to cell destruction. This, together with the non-selective cell toxicity associated with another lipophilic cation and known mitochondrial poison, dequalinium chloride (Gamboa-Vujicic, G., Emma, D. A., Liao, S. Y, Fuchtner, C. and Manetta, A. 1993. Toxicity of the mitochondrial poison dequalinium chloride in a murine model system. J Pharm Sci. 82:231-235), raises the importance of identifying class VI mitocans that are cancer cell-specific in terms of their uptake and cellular toxicity, as recently described in a predictive model based on their structures by Trapp, S. and Horobin, R. W. (2005. A predictive model for the selective accumulation of chemicals in tumor cells. Eur Biophys J. 34:959-966).

The amphipathic and positively charged $\alpha$-helical pro-apoptotic peptide $(KLAKLAK)_2$ has also been included in this class of mitocans as a delocalized lipophilic cation. However, the peptide must first be coupled to a targeted delivery system for surface receptor binding and uptake into cancer cells, before it is able to function as a mitocan (Ellerby, H. M., Arap, W., Ellerby, L. M.; Kain, R., Andrusiak, R., Rio, G. D., Krajewski, S., Lombardo, C. R., Rao, R., Ruoslahti, E., Bredesen, D. E. and Pasqualini, R. 1999. Anti-cancer activity of targeted pro-apoptotic peptides. Nat. Med. 5:1032-1038; Fantin et al. 2005). As with the other members of this class of mitocans, the peptide has been shown to dissipate $\Delta\Psi m,i$ leading to apoptosis, and it efficiently reduced tumour burdens in animal models (Fantin, V. R., Berardi, M. J., Babbe, H., Michelman, M. V., Manning, C. M. and Leder, P. 2005. A bifunctional targeted peptide that blocks HER-2 tyrosine kinase and disables mitochondrial function in HER-2-positive carcinoma cells. Cancer Res. 65:6891-6900):

SUMMARY OF THE INVENTION

The present inventors have now developed anti-cancer compounds that have a propensity to accumulate within the mitochondria of cancerous cells and induce the death of those cells. In one embodiment, such compounds comprise a pro-oxidant moiety attached to a mitochondrial delivery moiety. The pro-oxidant moiety generates reactive oxygen species within the mitochondria of cancerous cells and induces apoptosis of those cells. In another embodiment, such compounds comprise a pro-apoptotic moiety attached to a mitochondrial delivery moiety. The pro-apoptotic moiety induces apoptosis of those cells.

DETAILED DESCRIPTION OF THE INVENTION

According to a first aspect of the present invention, there is provided a compound for inducing the death of a cancerous cell, said compound comprising:

a pro-oxidant moiety for (i) generating reactive oxygen species within mitochondria of a cancerous cell and (ii) inducing apoptosis of the cancerous cell; and a delivery moiety for delivering the pro-oxidant moiety to the mitochondria of the cancerous cell.

According to a second aspect of the present invention, there is provided a compound for preventing or treating cancer, said compound comprising:

a pro-oxidant moiety for (i) generating reactive oxygen species within mitochondria of a cancerous cell and (ii) inducing apoptosis of the cancerous cell; and a delivery moiety for delivering the pro-oxidant moiety to the mitochondria of the cancerous cell.

According to a third aspect of the present invention, there is provided a method for inducing the death of a cancerous cell, said method comprising the step of administering to a subject a therapeutically effective amount of a compound comprising:

a pro-oxidant moiety for (i) generating reactive oxygen species within mitochondria of a cancerous cell and (ii) inducing apoptosis of the cancerous cell; and a delivery moiety for delivering the pro-oxidant moiety to the mitochondria of the cancerous cell.

According to a fourth aspect of the present invention, there is provided a method for preventing or treating cancer, said method comprising the step of administering to a subject a therapeutically effective amount of a compound comprising:

a pro-oxidant moiety for (i) generating reactive oxygen species within mitochondria of a cancerous cell and (ii) inducing apoptosis of the cancerous cell; and a delivery moiety for delivering the pro-oxidant moiety to the mitochondria of the cancerous cell.

According to a fifth aspect of the present invention, there is provided the use of a compound in the preparation of a medicament for inducing the death of a cancerous cell, said compound comprising:

a pro-oxidant moiety for (i) generating reactive oxygen species within mitochondria of a cancerous cell and (ii) inducing apoptosis of the cancerous cell; and a delivery moiety for delivering the pro-oxidant moiety to the mitochondria of the cancerous cell.

According to a sixth aspect of the present invention, there is provided the use of a compound in the preparation of a medicament for the prevention or treatment of cancer, said compound comprising:

a pro-oxidant moiety for (i) generating reactive oxygen species within mitochondria of a cancerous cell and (ii) inducing apoptosis of the cancerous cell; and a delivery moiety for delivering the pro-oxidant moiety to the mitochondria of the cancerous cell.

According to a seventh aspect of the present invention, there is provided a pharmaceutical or veterinary composition comprising the compound according to the first or second aspect of the present invention, or a physiologically acceptable salt thereof, and a physiologically acceptable carrier.

The compound may be in an isolated, purified, substantially purified, synthetic or recombinant form.

Any suitable type of delivery moiety may be used. Although the delivery moiety may target the pro-oxidant moiety to the intermembranous space, inner membrane or mitochondrial matrix of a mitochondrion, preferably the delivery moiety delivers the pro-oxidant moiety to the mitochondrial matrix of the cancerous cell.

Preferably, the delivery moiety is a lipophilic cation that selectively accumulates within the mitochondrial matrix of a cancerous cell due to the large membrane potential of the cancerous cell. A particularly preferred lipophilic cation is the triphenylphosphonium cation that is described in the specifications of International Patent Applications No. PCT/NZ98/00173 and PCT/NZ02/00154; and in James A M, Cochemé H M, Smith R A, Murphy M P. (Interactions of mitochondria-targeted and untargeted ubiquinones with the mitochondrial respiratory chain and reactive oxygen species. Implications for the use of exogenous ubiquinones as therapies and experimental tools. J Biol. Chem. 2005 Jun. 3; 280(22):21295-312. Epub 2005 Mar. 23.), the entire contents of which are hereby incorporated by cross-reference.

The tetraphenylphosphonium cation is another example of a suitable delivery moiety.

Other examples of suitable delivery moieties potentially include gold-phosphine or gold-carbine complexes as described in the publication by Barnard et al. (Barnard P J, Baker M V, Berners-Price S J, Day D A. Mitochondrial permeability transition induced by dinuclear gold(I)-carbene complexes: potential new antimitochondrial antitumour agents. J. Inorg. Biochem. 2004 October; 98(10):1642-7), the entire contents of which are hereby incorporated by cross-reference Yet other examples of suitable delivery moieties are described in Hoye, Adam T., Davoren, Jennifer E., Wipf, Peter, Fink, Mitchell P., and Kagan, Valerian E., (Targeting Mitochondria, Acc. Chem. Res., 41, 1, 87-97, 2008).

Any suitable type of pro-oxidant moiety may be used and the moiety may generate reactive oxygen species in any suitable way. Examples of preferred pro-oxidant moieties (mitocans) are listed in Table I above.

The compound may have more than one pro-oxidant moiety and the moieties may disrupt/target different regions/components of the respiratory chain.

Preferably, the pro-oxidant moiety interacts with mitochondrial complex II. More preferably, the pro-oxidant moiety binds to a ubiquinone-binding site of complex II and can readily displace the natural substrate ubiquinone, ubisemiquinone or ubiquinol (coenzyme Qs) or other quinones or related compounds preferentially interacting with complex II. Such substrates are specified, for example, in Briere J J, Schlemmer D, Chretien D, Rustin P. (2004) Quinone analogues regulate mitochondrial substrate competitive oxidation. Biochem Biophys Res Commun. April 16; 316(4):1138-42, Tan A K, Ramsay R R, Singer T P, Miyoshi H. (1993) Comparison of the structures of the quinone-binding sites in beef heart mitochondria. J Biol. Chem. September 15; 268 (26):19328-33, and Esposti M D, Ngo A, Ghelli A, Benelli B, Carelli V, McLennan H, Linnane A W (1996) The interaction of Q analogs, particularly hydroxydecyl benzoquinone (idebenone), with the respiratory complexes of heart mitochondria. Arch Biochem Biophys. June 15; 330(2):395-400.

Apoptosis may occur solely as a result of the increased levels of reactive oxygen species in the mitochondria of the cancerous cell, or the pro-oxidant moiety, delivery moiety or entire compound may be further pro-apoptotic by way of activating mitochondrial dependent cell death signalling pathways within the cell. Preferably, the pro-oxidant moiety generates reactive oxygen species by way of binding to complex II and is further pro-apoptotic by way of activating mitochondrial dependent cell death signalling pathways.

Preferably, the compound is cleaved, processed or otherwise metabolised in non-cancerous cells to a harmless form lacking pro-oxidant activity.

Preferably, the pro-oxidant moiety is a pro-oxidant vitamin E analogue. The present inventors have previously found that pro-oxidant vitamin E analogues can bind to complex II and disrupt electron transfer to ubiquinone. This has been described in the specification of International Patent Application No. PCT/AU2007/001371, the entire contents of which are incorporated herein by cross-reference. The inventors have also previously found pro-oxidant vitamin E analogues to be pro-apoptotic. The present inventors have further previously found that pro-oxidant vitamin E analogues can be processed to harmless anti-oxidant forms in non-cancerous cells.

A "pro-oxidant vitamin E analogue" is defined herein as a vitamin E analogue that, when located in mitochondria of a cancerous cell, is redox-silent and is capable of binding to a ubiquinone binding site of complex II and trigger the production of oxygen by-products of metabolism that can cause damage to the cell. An example of a pro-oxidant vitamin E analogue is α-tocopheryl succinate (α-TOS).

An "anti-oxidant vitamin E analogue", on the other hand, is a vitamin E analogue that has anti-oxidant (redox) activity when located in mitochondria of a cancerous cell, eg. α-tocopherol (α-TOH). Hence, the biological activities of pro-oxidant vitamin E analogue and anti-oxidant vitamin E analogue are directly opposed.

A preferred compound based on the triphenylphosphonium cation (designated Formula I) is shown below:

Formula I

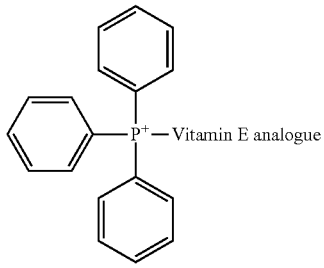

A particularly preferred compound based on the triphenylphosphonium cation and α-TOS (designated Formula II) is shown below:

Formula II

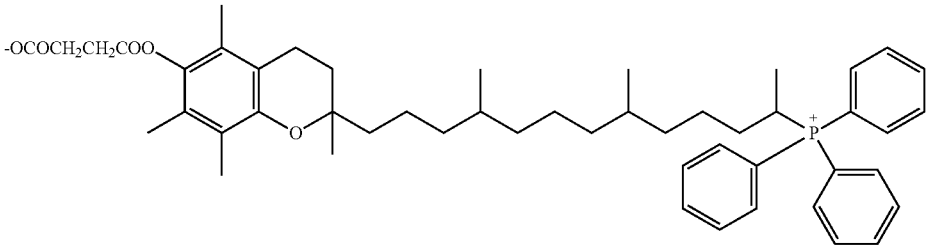

Other preferred compounds can be found in FIG. 1 of this specification.

The compound may be used to induce the death of any type of cancerous cell in a subject, eg. lung, liver, kidney, brain, prostate, breast, ovary, lymphoid, skin, eye, colon, gastric, oral squamous, and hematopoietic systems.

α-TOS has been previously found by the present inventors to efficiently kill erbB2-low or -high cancer cells. α-TOS has also been previously found by the inventors to treat mesothelioma. This has been described in the specification of International Patent Application No. PCT/AU2007/001371.

α-TOS has been previously found by the present inventors to induce the death of both normoxic and hypoxic cancerous cells. Thus, α-TOS has the advantage that it may be used to induce the death of both early and late stage tumours in a subject.

The subject for treatment may be a human, mammal or animal. Preferably, the subject is a human or other type of mammal.

The compound may be included in the composition as pharmaceutically or veterinarially acceptable derivatives thereof. As used herein "derivatives" of the compound includes salts, coordination complexes with metal ions such as $Mn^{2+}$ and $Zn^{2+}$, esters such as in vivo hydrolysable esters, free acids or bases, hydrates, or pro-drugs. Compounds having acidic groups such as phosphates or sulfates can form salts with alkaline or alkaline earth metals such as Na, K, Mg and Ca, and with organic amines such as triethylamine and Tris (2-hydroxyethyl)amine. Salts can also be formed between compounds with basic groups, such as amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques that will be well known to those of skill in the art.

The composition may be administered to the subject in either a prophylactically effective or a therapeutically effective amount as necessary for the particular situation under consideration. The actual amount of the compound in the composition and rate and time-course of administration of the composition, will depend on the nature and severity of the cancer being treated or the prophylaxis required. Prescription of treatment such as decisions on dosage and the like will be within the skill of the medical practitioner or veterinarian responsible for the care of the subject. Typically however, compositions for administration to a human subject will include between about 0.01 and 100 mg of the compound per kg of body weight and more preferably between about 0.1 and 10 mg/kg of body weight. When a compound comprising α-tocopheryl succinate or other analogue is applied transdermally to a human subject, the serum level of the compound is preferably in the vicinity of its $IC_{50}$ value, approximately 40-50 μM.

The composition may be administered to the subject in any suitable way, including: parenterally, topically, orally, by inhalation spray, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The carrier may comprise any suitable diluent, adjuvant, excipient, buffer, stabiliser, isotonicising agent, preservative or anti-oxidant. It will be appreciated that the carrier should be non-toxic and should not interfere with the efficacy of the compound. The precise nature of the carrier or any other additive to the composition will depend on the route of administration and the type of treatment required. See, for example, Alfonso R. Gennaro. Remington: The Science and Practice of Pharmacy, 20th Edition. Baltimore, Md.: Lippincott Williams & Wilkins, 2000, and Goodman and Gilman's The Pharmaceutical Basis of Therapeutics, Pergamon Press, New York, N.Y., the entire contents of which are incorporated herein by reference. Pharmaceutical compositions may be produced, for instance, by means of conventional mixing, dissolving, granulating, dragee-making, levigating, emulsifying, encapsulating, entrapping or lyophilizing processes.

Sterile injectable forms of the composition may be aqueous or oleaginous suspension. Such forms will be known to those of skill in the art. For intravenous, cutaneous or subcutaneous injection, or injection at a site where treatment is desired, the composition may be in the form of a parenterally acceptable aqueous solution which has suitable pH, isotonicity and stability.

Orally acceptable dosage forms of the composition include capsules, tablets; pills, powders, liposomes, granules, spheres, dragees, liquids, gels, syrups, slurries, suspensions and the like. Suitable oral forms will be known to those of skill in the art. A tablet can include a solid carrier such as gelatine or an adjuvant or an inert diluent. Liquid pharmaceutical compositions generally include a liquid carrier such as water, petroleum, animal or vegetable oils, a mineral oil or a synthetic oil. Physiological saline solution, or glycols such as ethylene glycol, propylene glycol or polyethylene glycol may be included. Such compositions and preparations will generally contain at least 0.1 wt % of the compound and preferably up to about 25 wt %, depending on its solubility in the given carrier.

The composition may be administered topically, especially when the target of treatment includes areas or organs readily accessible by topical application, including cancers of the eye, the skin, or the lower intestinal tract. The composition may be applied in the form of a solution, suspension, emulsion, ointment, cream, lotion, paste, gel, foam, or aerosol. Suitable topical forms will be known to those of skill in the art.

The composition may include a delivery vehicle for delivering the compound to a particular organ, tissue or type of cancer, and/or for ensuring that the compound is able to be, for instance, absorbed through the skin or ingested through the gut without loss of biological efficacy. Delivery vehicles may comprise, for example, lipids, polymers, liposomes, emulsions, antibodies and/or proteins. Liposomes are particularly preferred for delivering the compound through the skin to, say, treat mesothelioma.

The composition may be delivered using a sustained-release system, such as semipermeable matrices of solid hydrophobic polymers containing the compound. Various sustained-release materials are available and well known by those skilled in the art. Sustained-release capsules may, depending on their chemical nature, release the compound for about 1 to 20 weeks.

The compound may be in the form of a pro-drug. The pro-drug may have protective groups such that the activity of the compound is not compromised when the composition is taken, say, orally. The pro-drug may deliver the active compound to a particular organ or cell type. Suitable pro-drug forms and protective groups will be known to those of skill in the art. Preferably, an adduct of α-TOS is linked to the heptapeptide LTVSPWY, for targeting cancer cells over-expressing the receptor tyrosine kinase, erbB2.

A subject may be administered the composition comprising the compound together with one or more other actives to achieve an optimal prophylactic or therapeutic effect. The actives may be, for example, alkylating agents, angiogenesis inhibitors, anti-androgens, anti-estrogens, anti-metabolites, apoptosis agents, aromatase inhibitors, cell cycle controlling agents, cell stressor, cytotoxics, cytoprotectant, hormonals, immunotherapy agents, kinase inhibitors, monoclonal antibodies, platinum agents, a respiratory inhibitor, retinoid, signal transduction inhibitors, taxanes and topoisomerase inhibitors. Particularly preferred agents include glycolytic inhibitors such as 2-deoxyglucose and 3-BP. Other particularly preferred agents include TRAIL and Aka1 inhibitors, as well as other mitocans as reviewed in Ralph S J, Dong L F, Low P, Lawen A, and Neuzil J (2006) Mitocans: mitochondria targeted anti-cancer drugs as improved therapies and related patents. Recent Pat Anticancer Drug Discov 1:305-326; Neuzil J, Doug L F, Ramanathapuram L, Hahn T, Chladova M, Wang X F, Zobalova R, Prochazka L, Gold M, Freeman R, Turanek J, Akporiaye E T, Dyason J C, Ralph S J. (2007) Vitamin E analogues as a novel group of mitocans: Anti-cancer agents that act by targeting mitochondria. Mol Aspects Med. February 23; and Neuzil J, Tomasetti M, Zhao Y, Dong L F, Birringer M, Wang X F, Low P, Wu K, Salvatore B A, Ralph S J. (2007) Vitamin E analogs, a novel group of "mitocans," as anticancer agents: the importance of being redox-silent. Mol. Pharmacol. May; 71(5):1185-99, the entire contents of which are incorporated herein by way of cross-reference.

The present inventors previously have found, for example, that cancer cells are rendered more sensitive to killing by the combination of α-TOS and 3-BP (as well as with other drug combinations) compared with either drug used alone.

Preferably, the composition is administered parenterally or topically. The particularly preferred pro-oxidant vitamin E analogue moieties are α-tocopheryl succinate, α-tocopheryl maleate, α-tocopheryl maleyl amide, and 2,5,7,8-tetramethyl-2R-(4R,8R,12-trimethyltridecyl)-chroman-6-yloxyacetic acid (α-tocopheryloxyacetic acid). The preferred carrier for the esters α-tocopheryl succinate, α-tocopheryl maleate and α-tocopheryl maleyl amide is a transdermally applicable cream, such as the liposome-based cream "Lipoderm". The non-hydrolysable ether analogue, α-tocopheryloxyacetic acid, is preferably delivered orally.

According to an eighth aspect of the present invention, there is provided a compound for inducing the death of a cancerous cell, said compound comprising:

a pro-apoptotic moiety for inducing apoptosis of a cancerous cell; and a delivery moiety for delivering the pro-apoptotic moiety to mitochondria of the cancerous cell.

According to a ninth aspect of the present invention, there is provided a compound for preventing or treating cancer, said compound comprising:

a pro-apoptotic moiety for inducing apoptosis of a cancerous cell; and a delivery moiety for delivering the pro-apoptotic moiety to mitochondria of the cancerous cell.

According to a tenth aspect of the present invention, there is provided a method for inducing the death of a cancerous cell, said method comprising the step of administering to a subject a therapeutically effective amount of a compound comprising:

a pro-apoptotic moiety for inducing apoptosis of a cancerous cell; and a delivery moiety for delivering the pro-apoptotic moiety to mitochondria of the cancerous cell.

According to an eleventh aspect of the present invention, there is provided a method for preventing or treating cancer, said method comprising the step of administering to a subject a therapeutically effective amount of a compound comprising:

a pro-apoptotic moiety for inducing apoptosis of a cancerous cell; and a delivery moiety for delivering the pro-apoptotic moiety to mitochondria of the cancerous cell.

According to a twelfth aspect of the present invention, there is provided a pharmaceutical or veterinary composition comprising the compound according to the eighth or ninth aspect of the present invention, or a physiologically acceptable salt thereof, and a physiologically acceptable carrier.

The compound may be in an isolated, purified, substantially purified, synthetic or recombinant form.

Any suitable type of delivery moiety may be used. The delivery moiety may be as described above.

Any suitable type of pro-apoptotic moiety may be used. Preferably, the pro-apoptotic moiety is a pro-oxidant moiety as described above. Examples of preferred pro-oxidant moieties (mitocans) are listed in Table I above as well as in Tables II-IV and FIG. 1.

The compounds used were α-TOH, α-TOS, $VE_{11}S$ (hereafter referred to as "VES"), Mito $VE_3S$, Mito $VE_3S$, Mito $VE_7S$, Mito $VE_9S$ and Mito $VE_{11}S$ (hereafter referred to as "MitoVES"), Mito $VE_{11}AE$ (hereafter referred to as "Mito VEAE"), Mito $VE_{11}F$ [not shown] (hereafter referred to as "MitoVEF"), Mito$VE_{11}M$ [not shown] (hereafter referred to as "MitoVEM"), and VES4TPP. α-TOH and α-TOS were obtained from Sigma, VES, MitoVES, MitoVEAE, MitoVEF, MitoVEM and VES4TPP were synthesised as described in the section entitled General Materials and Methods.

Figure 2:
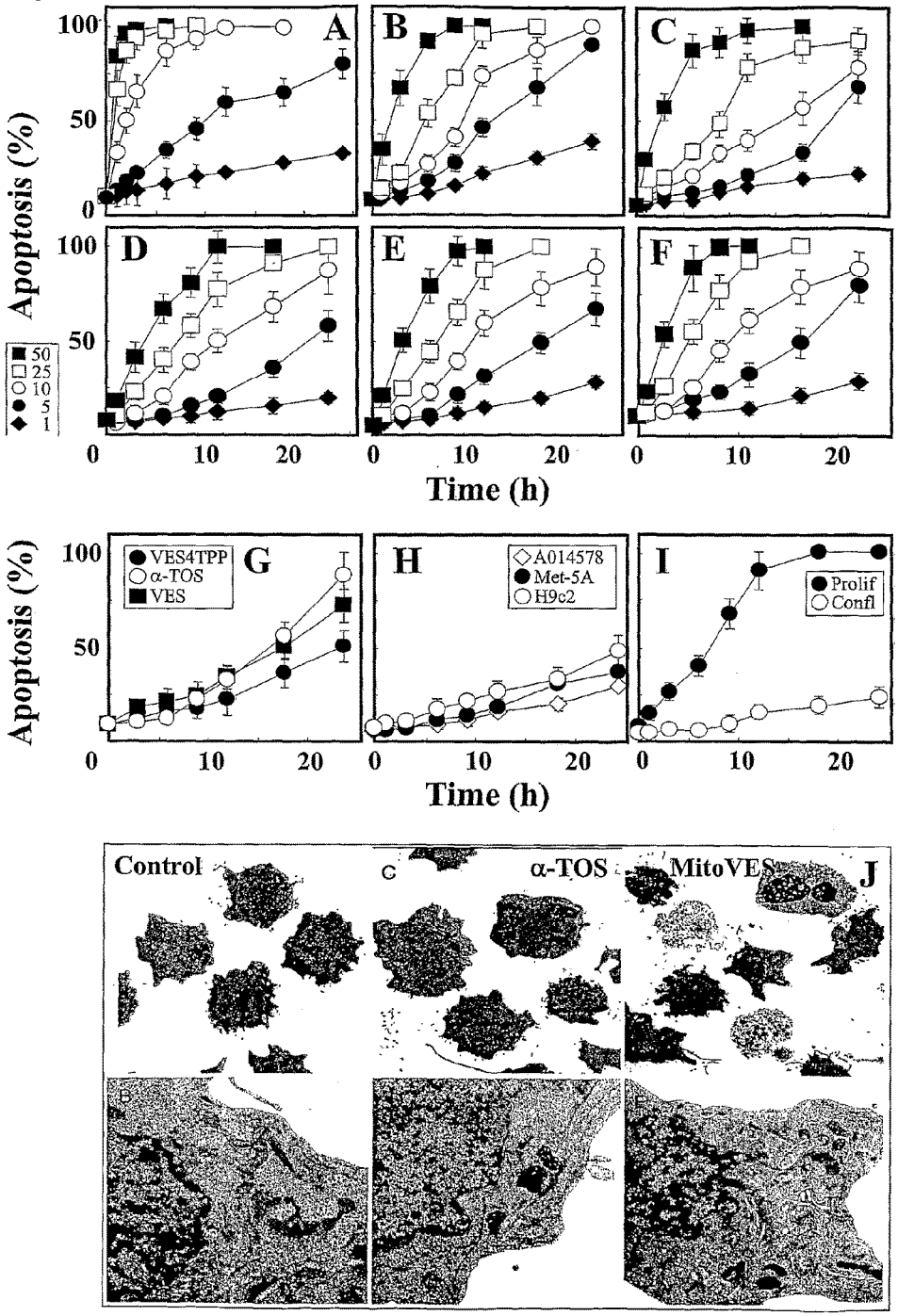

FIG. 2. MitoVES causes apoptosis selectively in malignant cells.

Jurkat (A, G), HCT-116 (B), MCF-7 (C), MDA-MB-453 (D), and Meso-2 cells (E) were exposed to MitoVES at concentrations 1-50 μM (A-F), or to VES4TPP or α-TOS at 50 μM (B). At the times shown, the cells were harvested and assessed for apoptosis. Panel H shows the A014578 or 40% confluency for the times shown and assessed for apoptosis. Panel J shows TEM of control Jurkat cells or the cells exposed to 50 μM α-TOS or 5 μM MitoVES (upper panels at lower magnification and lower panels at higher magnification). Apoptosis data shown are derived from three independent experiments and are presented as mean values±S.D., the micrographs are representative images of at least three independent experiments.

Figure 3A:
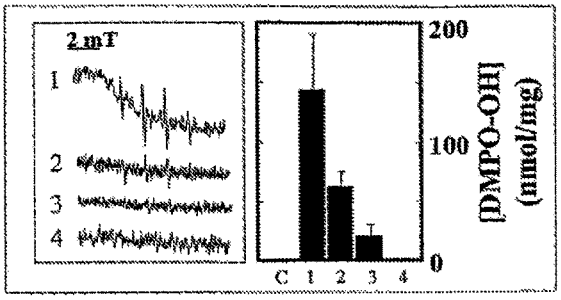

FIG. 3. Apoptosis triggered by MitoVES is dependent on ROS and the intrinsic pathway.

3A—Production of oxygen radicals induced by MitoVES measured by electron paramagnetic resonance spectroscopy (EPR) (left hand panel) as, well as by using the fluorescent dye indicator DMPO (right hand panel).

3B—Parental, $Bax^{-/-}$ and $Bax^{-/-}$ Jurkat cells were exposed to α-TOS (T) at 50 μM and MitoVES (M) 5 μM, and apoptosis assessed.

Figure 4A:
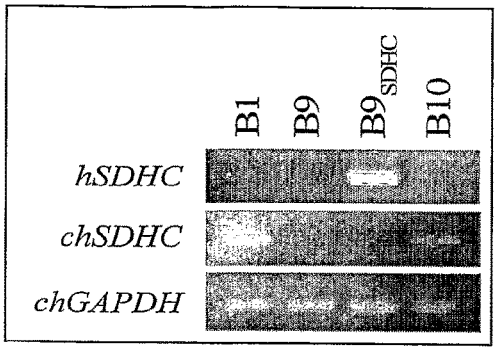
Figure 4B:
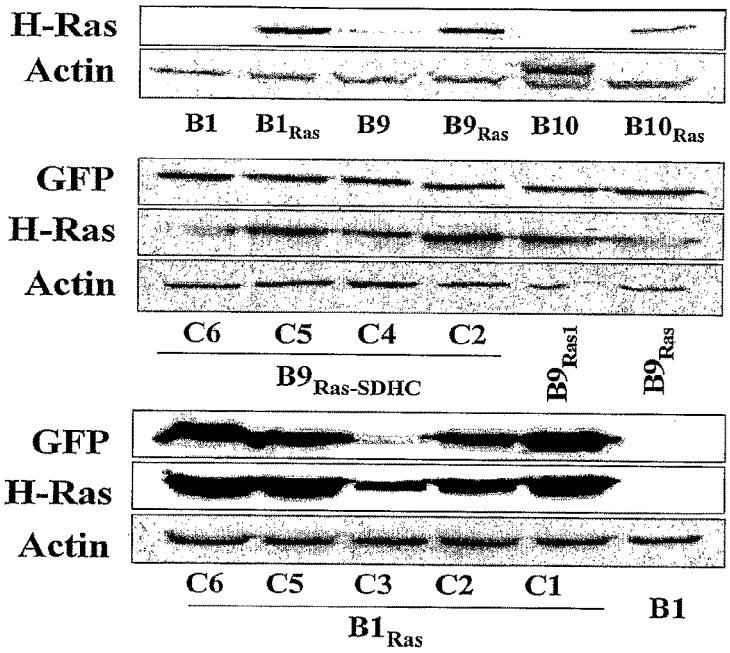

FIG. 4. MitoVES accumulates in the inner mitochondrial membrane and interferes with the coenzyme Q binding site of complex II.

4A—RT-PCR, of Ras-transformed B1, B9 and B 10 Chinese hamster lung fibroblast cell lines, for hSDHC and chSDHC mRNA expression.

4B—Western blotting analysis of B1, B9 and B10 Chinese hamster lung fibroblast cell lines with relevant antibodies to detect protein levels of expression as shown. The results are from clonally selected Ras transformed $B1_{Ras}$ and $B9_{Ras\text{-}SDHC}$ sub lines, positive for Ras and GFP fusion protein expression and comparison is made with samples from the parental non-transformed B1, B9 and B10 cells.

4C—After 24 h of treatment with Complex II targeting drugs TTFA or MitoVES, Ras transformed B1 and B9 cells were assessed for apoptosis using the Annexin V binding method.

Figure 5:
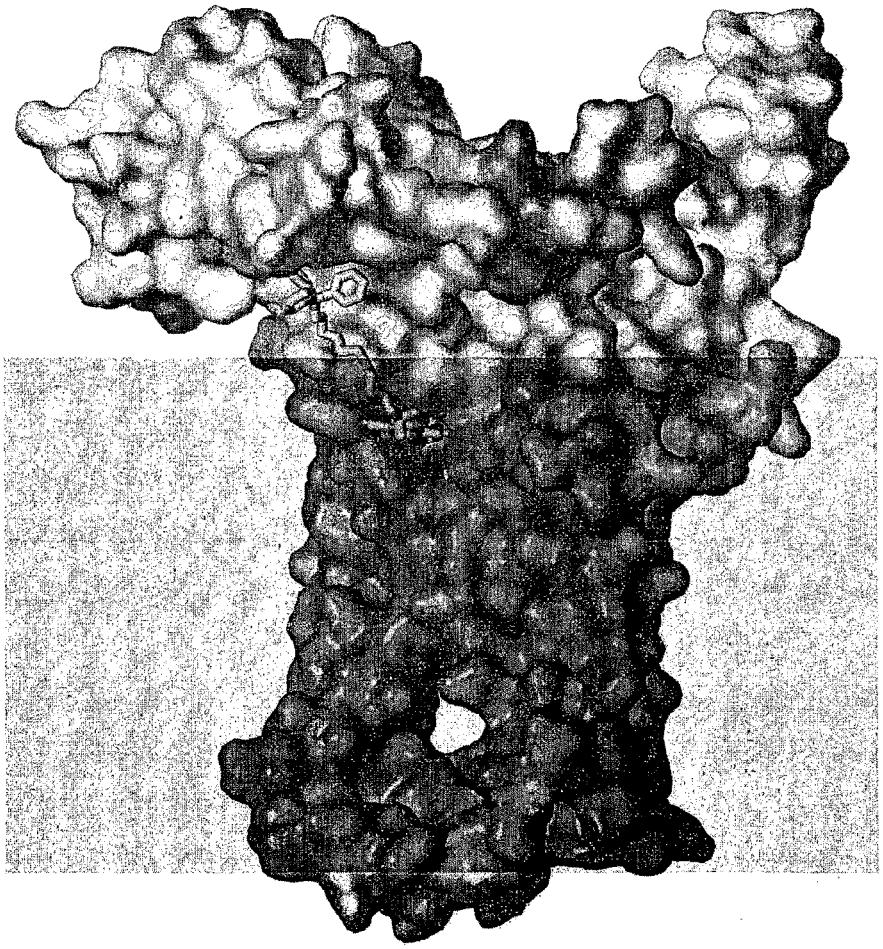

FIG. 5. Molecular modelling of MitoVES binding in Complex II.

Space filling model of Complex II with MitoVES (identified as a stick figure structure) produced using AutoDock (Morris G M, Goodsell D S, Halliday R S, Huey R, Hart W E, Belew R K, Olson A J (1998) Automated docking using a Lamarckian genetic algorithm and empirical binding free energy function, J Comp Chem 19: 1639-1662) and Astex Viewer (Hartshorn M J (2002) AstexViewer™: An aid for structure-based drug design. J Computer Aided Mol Des 16: 871-881). The surface of Chain B (iron-sulfur protein) of Complex II and the surfaces of Chains C and D (the transmembrane section) are shown, but Chain A (flavoprotein-succinate reductase) is not shown.

Figure 6:
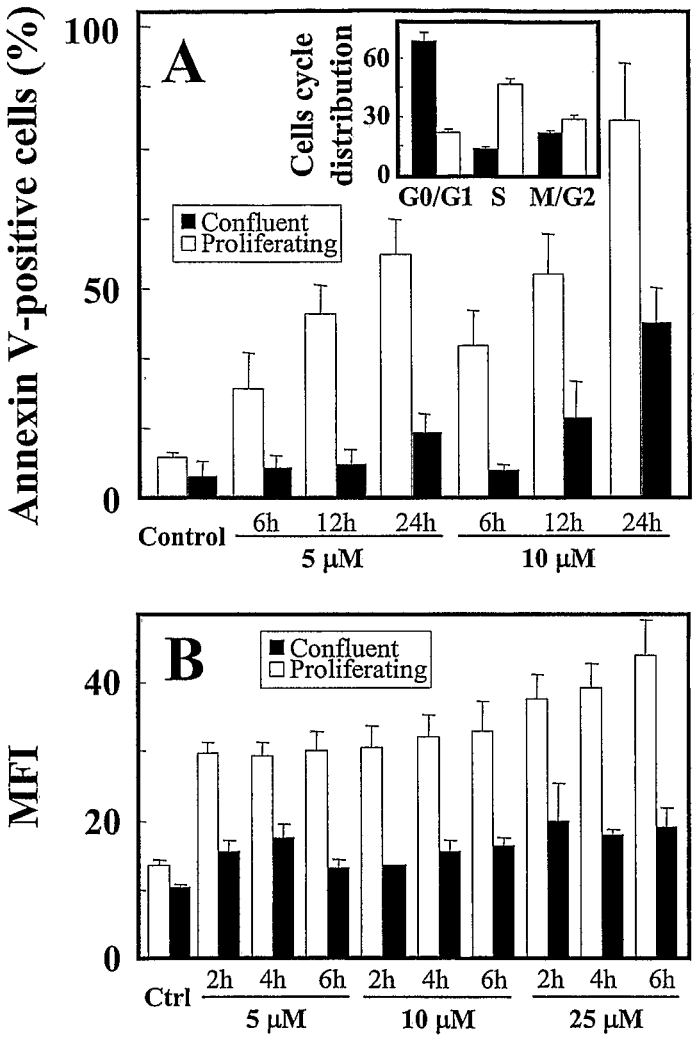

FIG. 6. MitoVES causes apoptosis in proliferating but not arrested endothelial cells due to accumulation of ROS.

Parental EAhy926 cells were seeded in 24-well plate so that they would acquire after an overnight recuperation ~50% or 100% confluency, while their $\rho^0$ counterparts were seeded at 50% confluency. The proliferating and confluent cells were then exposed to MitoVES at concentrations and for times shown, and assessed for apoptosis level by the Annexin V-binding method (A) and for ROS accumulation using the fluorescent probe DHE (B). The inset in panel A shows the cell cycle distribution in proliferating and confluent EAhy926 cells. Panel C shows ROS accumulation in proliferating and confluent EAhy926 cells using EPR spectroscopy.

Figure 7:
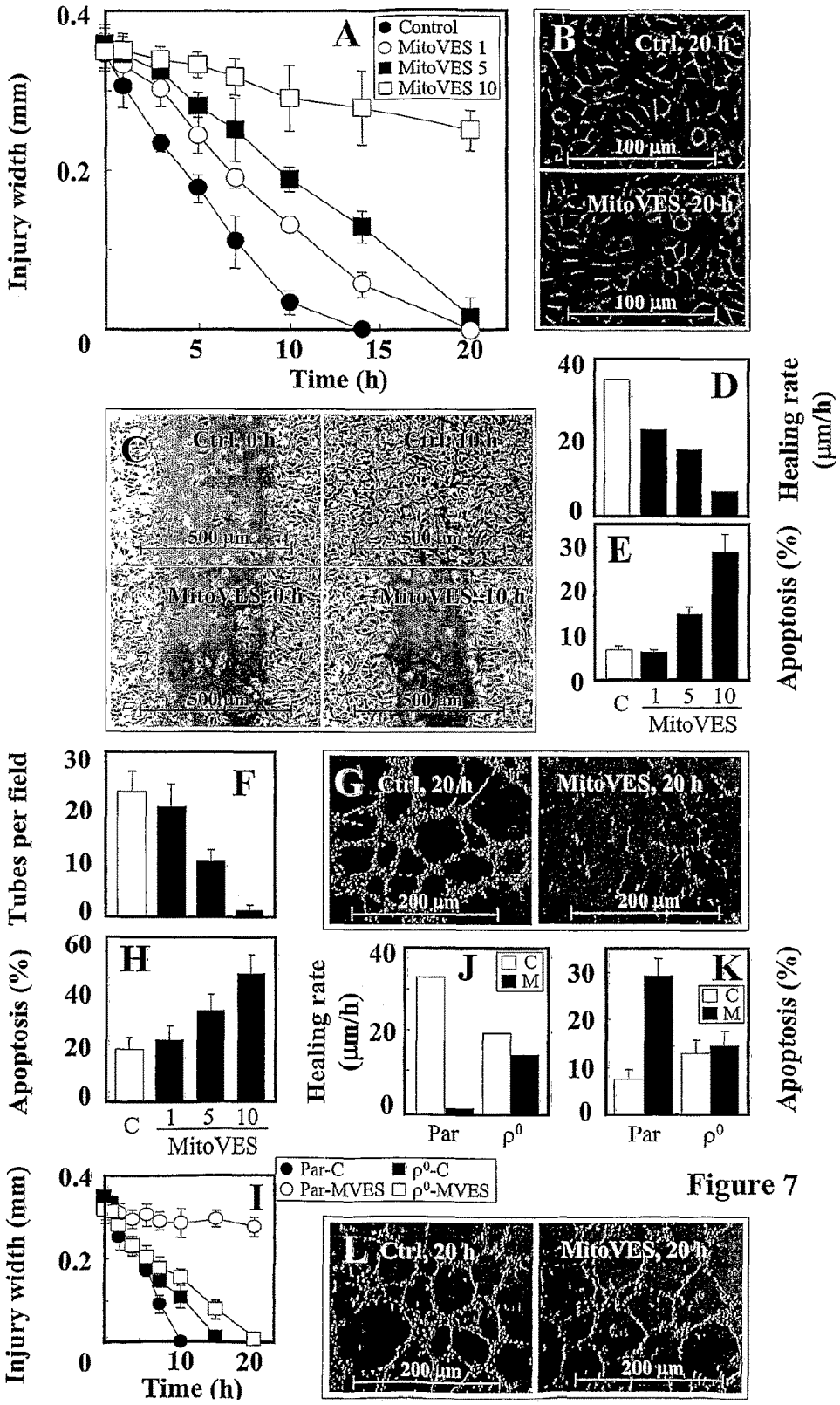

FIG. 7. MitoVES inhibits angiogenesis in vitro.

Wound-healing (A-F) and tube-forming activity (G, H) were assessed using the EC EAhy926 cells. For wound-healing activity, the cells were seeded in 35-mm Petri dishes and allowed to reach 100% confluency. The 'injury' was then performed, resulting in a denuded gap of 0.4-0.5 mm. Wound-healing activity in control cells and cells supplemented with 1, 5 or 10 μM MitoVES was assessed on the basis of proliferation and migration of cells into the denuded zone using a light microscope equipped with a grid and a digital camera (A). Panel B shows morphology of the cells in zones of arrested ECs 20 h after the injury for the control culture and from cells exposed to 10 μM MitoVES. In panel C, representative images of injured control cells and cells treated with 10 μM MitoVES at different times are presented. Panel D shows the healing rate for the different conditions derived from the slopes of the individual curves in panel A. In panel E, the level of apoptosis is shown at 20 h after the injury for control cultures and for cells exposed to MitoVES. EAhy926 cells were seeded at ~$10^5$ per well in Matrigel-coated 24-well plates and allowed for 24 h to form tubes at the absence or presence of MitoVES. Complete capillaries connecting points of individual polygons (see General Materials and Methods) were counted per the field of 0.16 $mm^2$ and took as a measure of the tube-forming activity (F). Panel G shows representative images of the Matrigel cultures of control cells and cells treated for 20 h with 5 μM MitoVES. At 20 h of treatment, the cells were retrieved from the Matrigel and assessed for apoptosis using the Annexin V binding method (H). Parental EAhy926 cells and their $\rho^0$ counterparts were seeded in Petri dishes at confluency, 'injured' as described above, and the wound-healing activity assessed in the absence or presence of 10 μM MitoVES (MVES) (I; see symbols above panel L). The healing rate was estimated from the slopes in panel I and plotted in mmol/h (J). At 20 h, the cells were assessed for the level of apoptosis (K). Panel L documents tube-forming activity in Matrigel of the $\rho^0$ EAhy 926 cells in the absence or presence of 5 μM MitoVES. Data shown are derived from three independent experiments and are presented as mean values±S.D., the micrographs are representative images of at least three independent experiments.

Figure 8:
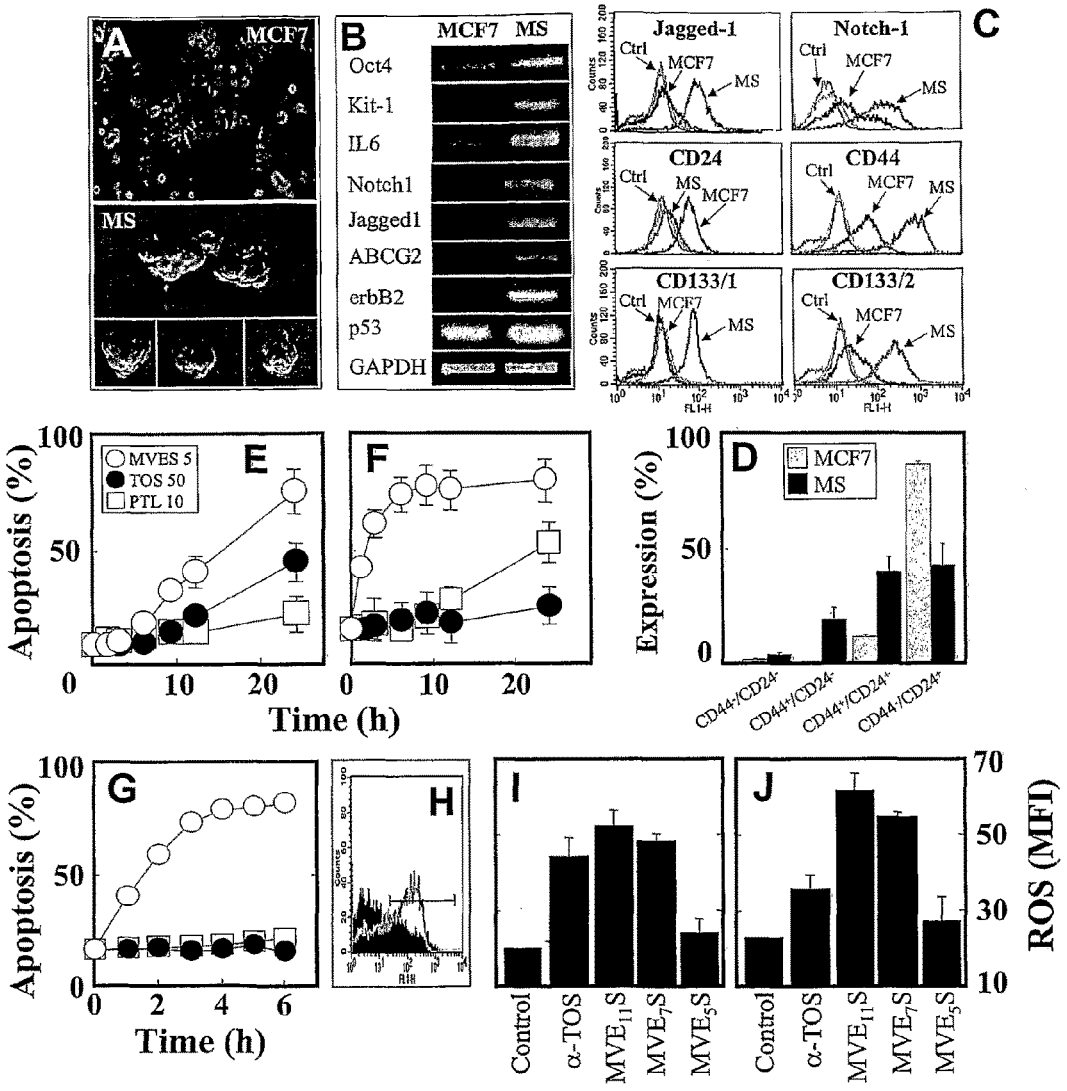

FIG. 8. MitoVES is a highly effective drug for killing populations of the human breast cancer cell line, MCF7, enriched for cancer stem cells.

Adherent MCF7 cells and the corresponding mammosphere cells (MS) were cultured and assessed for morphological changes by microscopy (A) and for expression levels of markers as indicators of "sternness" by RT-PCR (B) and flow cytometry (C), including the expression of CD44 and CD24 (D). The adherent MCF7 cells (E) and the MS cells (F) were treated with 5 μM MitoVES, 50 μM α-TOS or 10 μM parthenolide and assessed for their sensitivity to drug induced cell death. Panel G shows the initial levels of cell death by apoptosis in MS cells exposed to MitoVES and panel H shows the histogram analysis of the MS cells exposed to 5 μM MitoVES for 3 h and then analysed for annexin V-FITC binding. Adherent MCF7 cells (I) and MS cells (J) were treated for 3 h with α-TOS (50 μM) or MitoVES homologues containing different lengths in the aliphatic side chain (5 μM each, either 11, 7 or 5 carbon chain in length) and the treated cells assessed for production of reactive oxygen species (ROS) by flow cytometry.

Figure 9:
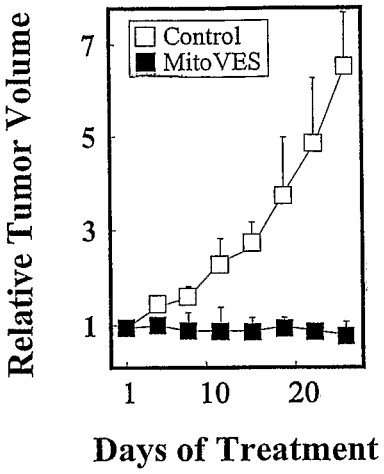

FIG. 9. MitoVES treatment completely blocks progression of breast cancer tumours in transgenic FVB/N c-neu mice that form spontaneous ductal breast carcinomas.

The transgenic FVB/N c-neu female mice with spontaneous small breast carcinomas were treated with MitoVES at 3 μmol per mouse per dose and the tumour volume was assessed by repeated ultrasound imaging, monitoring tumour growth over several weeks.

EXAMPLES

In order that this invention may be better understood, the following examples are set fourth. These examples are for the purpose of illustration only and are not to be construed as limiting the scope of the invention in any manner.

General Materials and Methods

Cell Culture.

The following cell lines used in this study were obtained from ATCC, unless specified otherwise: Human T lymphoma cells Jurkat, human mesothelioma cells Meso-I, MM-BI, Ist-Mes, Ist-Mes-2 (Pass, H. I. et al. Characteristics of nine newly derived mesothelioma cell lines. Ann. Thorac. Surg. 59, 835-844 (1995)), human breast cancer cells MCF-7 (erbB2-low) and MDA-MB-453 (erbB2-high), human colorectal cells HCT-116, human hepatocarcinoma cells Huh-7, mouse mesothelioma cells AE17 (Jackaman, C. et al. IL-2 intratumoral immunotherapy enhances CD8+ T cells that mediate destruction of tumor cells and tumor-associated vasculature: a novel mechanism for IL-2. J. Immunol. 171, 505150-505163 (2003), human non-malignant mesothelial cells Met-5A, rat ventricular myocyte-like cells HL-1 (Claycomb, W. C. et al. HL-1 cells: a cardiac muscle cell line that contracts and retains phenotypic characteristics of the adult cardiomyocyte. Proc. Natl. Acad. Sci. USA 95, 2979-2984 (2001)) and H9c2, and the human endothelial-like cells EAhy926 (Edgell, C. J., McDonald, C. C. & Graham, J. B. Permanent cell line expressing human factor VIII-related antigen established by hybridization. Proc. Natl. Acad. Sci. USA 80, 3734-3737 (1983)). Jurkat cells were grown in the RPMI medium while DMEM was used for other malignant cell lines and for Met-5A cells, supplemented with 10% FCS and antibiotics. HL-1 cells, maintained in fibronectin/gelatine-coated dishes, were grown in the Claycomb medium supplemented with noradrenalin (Claycomb, W. C. et al. HL-1 cells: a cardiac muscle cell line that contracts and retains phenotypic characteristics of the adult cardiomyocyte. Proc. Natl. Acad. Sci. USA 95, 2979-2984 (2001)), EAhy926 cells were grown in complete DMEM supplemented with HAT (Edgell, C. J., McDonald, C. C. & Graham, J. B. Permanent cell line expressing human factor VIII-related antigen established by hybridization. Proc. Natl. Acad. Sci. USA 80, 3734-3737 (1983)). Cells deficient in mtDNA ($\rho^0$ phenotype) were prepared as detailed in Weber, T. et al., (Mitochondria play a central role in apoptosis induced by α-tocopheryl succinate, an agent with anticancer activity. Comparison with receptor-mediated pro-apoptotic signaling. Biochemistry 42, 4277-4291 (2003)). Acquisition of the $\rho^0$ phenotype was confirmed by lack of expression by the cells of the mtDNA-encoded cytochrome c oxidase subunit II (COXII not shown). Chinese hamster lung fibroblasts deficient in complex I (B10 cells) (See, B. B. et al. Molecular remedy of complex I defects: rotenone-insensitive internal NADH-quinone oxidoreductase of Saccharomyces cerevisiae mitochondria restores the NADH oxidase activity of complex I-deficient mammalian cells. Proc. Natl. Acad. Sci. USA 95, 9167-9171 (1998)) and complex II ($CybL^{-/-}$; B9 cells) (Oostveen, F. G., Au, H. C., Meijer, P. J. & Scheffler, I. E. A Chinese hamster mutant cell line with a defect in the integral membrane protein CII-3 of complex II of the mitochondrial electron transport chain. J. Biol. Chem. 270: 26104-26108 (1995)) as well as the parental cells (B1 cells) (Oostveen, F. G., Au, H. C., Meijer, P. J. & Scheffler, I. E. A Chinese hamster mutant cell line with a defect in the integral membrane protein CII-3 of complex II of the mitochondrial electron transport chain. J. Biol. Chem. 270: 26104-26108 (1995)) were grown in DMEM with 10% FCS, antibiotics, 10 mg/ml glucose and non-essential aminoacids.

Synthesis of VE Analogs.

Figure 1:
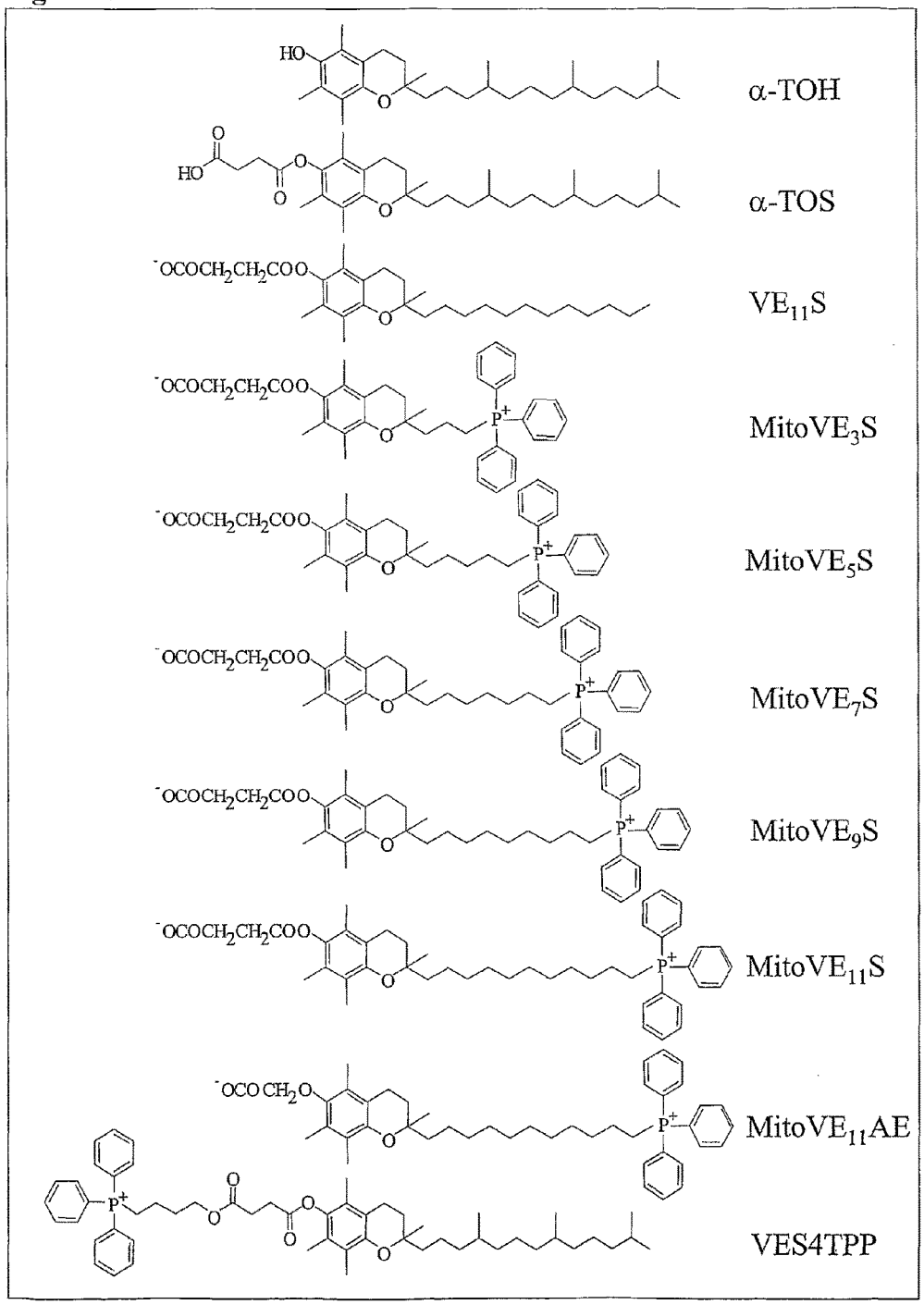
FIG. 1. Compounds used in the study.

The following compounds (most of which are shown in FIG. 1) were generally synthesised according to a method described in the specifications of International Patent Applications No. PCT/NZ98/00173 and PCT/NZ02/00154: —MitoVE$_{11}$S, S-MitoVE$_{11}$S, R-MitoVE$_{11}$S, MitoVE$_9$S, MitoVE$_7$S, MitoVE$_5$S, MitoVE$_3$S, MitoVE$_{11}$AE, MitoVE$_{11}$F and VES4TPP.

Assessment of IC$_{50}$, Apoptosis and Mitochondrial Potential.

Toxicity of α-TOS, VE$_{11}$S ("VES"), MitoVE$_3$S, MitoVE$_5$S, MitoVE$_7$S, MitoVE$_9$S, MitoVE$_{11}$S ("MitoVES"), MitoVE$_{11}$AE ("MitoVEAE"), MitoVE$_{11}$F ("MitoVEF"), MitoVE$_{11}$M ("MitoVEM"), and VES4TPP towards cancer cells was assessed on the basis of IC$_{50}$, as detailed in Turanek, J., et al. ((2008). Liposomal formulation of vitamin E analogs as an efficient and selective anti-cancer treatment. Clin. Cancer Res. (submitted)). Apoptosis was assessed using the Annexin V method (Weber, T. et al. Mitochondria play a central role in apoptosis induced by α-tocopheryl succinate, an agent with anticancer activity. Comparison with receptor-mediated pro-apoptotic signaling. Biochemistry 42, 4277-4291 (2003)) and dissipation of the mitochondrial inner transmembrane potential was estimated using the polychromatic probe JC-1 (Molecular Probes) (Weber, T. et al. Mitochondria play a central role in apoptosis induced by α-tocopheryl succinate, an agent with anticancer activity. Comparison with receptor-mediated pro-apoptotic signaling. Biochemistry 42, 4277-4291 (2003)).

Evaluation of Cell Proliferation, and Cell Cycle Distribution.

Cell proliferation was determined, using an ELISA colorimetric kit (Roche) to determine the number of cells in S phase of the cell cycle, based on DNA incorporation of 5-bromo-2-deoxyuridine (BrdUrd) using the manufacturer's protocol. For cell cycle analysis, cells were plated in 24-well plates so that they reached ~50%, 70%, and 100% confluency after 24-h recuperation. Cells were then harvested and resuspended in buffer containing sodium citrate (1%), Triton X-100 (0.1%), RNase A (0.05 μg/mL), and propidium iodide at 5 μg/mL, incubated in the dark for 30 min at 4° C. and analyzed by flow cytometry.

Assessment of SDH Activity.

A time course for the reduction of the complex II substrate 2,6-dichlorophenol indophenol (DCIP) by the mitochondrial preparations was followed by measuring the absorbance at 600 nm in 1 cm cuvettes containing a 1 ml reaction volume ($\epsilon_{600}$=21×10$^3$ M$^{-1}$ cm$^{-1}$). The reaction components included NADH, 0.5 mM; succinate, 5 mM; KCN, 10 mM; DCIP, 50 μM; phenazine methosulphate (PMS), 50 μM. For each assay point, 0.5 mg sample protein was used and α-TOS was added at either 100 or 300 μM as indicated. The change in absorbance of DCPIP was measured using a spectrophotometer (UVIKON XL, Secomam) and replicate samples were assayed (n=3). When measuring the complex I (NADH dehydrogenase activity), PMS was omitted. For the control reactions without α-TOS, the diluent DMSO was added so that its final concentration was <0.1% (v/v).

ROS Accumulation Assessment.

Cellular ROS were detected indirectly by flow cytometry and directly by electron paramagnetic resonance (EPR) spectroscopy, following treatment of cells with α-TOS as indicated in the Legend to Figures. In some experiments, the cells were pre-treated for 1 h with 2 μM mitochondrially targeted coenzyme Q (MitoQ) (Kelso, G. F., et al. Selective targeting of a redox-active ubiquinone to mitochondria within cells: antioxidant and antiapoptotic properties. J. Biol. Chem. 276, 4588-45896 (2001)) or co-incubated with superoxide dismutase (SOD; Sigma S4636; EC 1.15.1.1) at 750 units per ml. For indirect evaluation, cells were treated with α-TOS and reacted with dihydrodichlorofluorescein diacetate (DCF; Molecular Probes) for 30 min, and scored by flow cytometry for cells with high fluorescence, which was evaluated on the bases on increase in mean fluorescence intensity. EPR spectroscopy analysis of ROS generation was based on the use of the radical trap 5,5-dimethyl-1-pyrroline N-oxide (DMPO; Sigma). In brief, cells were plated in T25 flasks and allowed to reach 60-70% confluency (~5×10$^6$ cells per flask). Cells were washed, overlayed with the PSS medium (Thomas, S. R., Chen, K., & Keaney, J. F. Hydrogen peroxide activates endothelial nitric-oxide synthase through coordinated phosphorylation and dephosphorylation via a phosphoinositide 3-kinase-dependent signaling pathway. J Biol. Chem. 277, 6017-6024 (2002)) and incubated with 50 μM α-TOS 5 min after addition of 10 mM DMPO. Analyses of DMPO adducts were performed with samples taken from the cell suspension as well as the cell-conditioned medium transferred into a quartz flat cell (Wilmad). The quartz cell was then placed into the cavity of the Bruker EMX bench-top spectrometer set at 293 K with the following spectrometer parameters: field sweep 10 mT, microwave power 20 mW, microwave frequency 100 kHz, modulation amplitude, 0.1 mT, sweep time 83.9 s. The detection limit of the stable nitroxide (TEMPO) under identical conditions was ~50 nM.

Cell Transfections.

B9 cells were transfected using the Topo pCR3.1 Uni plasmid harbouring the CybL gene (Slane B G, Aykin-Burns N, Smith B J, Kalen A L, Goswami P C, Domann F E, Spitz D R. (2006). Mutation of succinate dehydrogenase subunit C results in increased oxidative stress, and genomic instability. Cancer Res 66: 7615-7620) and selected as described (Weber T, Dalen H, Andera L, Negre-Salvayre A, Auge N, Sticha M et al. (2003). Mitochondria play a central role in apoptosis induced by α-tocopheryl succinate, an agent with anticancer activity. Biochemistry 42: 4277-4291). Stably transfected and siRNAtreated cells were assessed for SDH activity and SDHC expression. Western blotting was performed as described (Wang X F, Birringer M, Dong L F, Veprek P, Low P, Swettenham E et al. (2007). A peptide adduct of vitamin E succinate targets breast cancer cells with high erbB2 expression. Cancer Res 67: 3337-3344) using anti-SDHC immunoglobulin G (IgG) (clone 3E2; Novus Biologicals) with anti-β-actin IgG (Santa Cruz Biotechnology, Santa Cruz, Calif., USA) as a loading control. RT-PCR was performed using a standard protocol. The published human CybL (Slane B G, Aykin-Burns N, Smith B J, Kalen A L, Goswami P C, Domann F E, Spitz D R. (2006). Mutation of succinate dehydrogenase subunit C results in increased oxidative stress, and genomic instability. Cancer Res 66: 7615-7620) and Chinese hamster glyceraldehyde 3-phosphate dehydrogenase primers (Sever et al., 2004) were used.

Assessment of Angiogenesis In Vitro.

To assess the effect of α-TOS on the wound-healing activity of the EAhy926 cells, the cells were seeded in 3.5 mm Petri dishes and allowed to reach complete confluence. Using a sterile yellow pipette tip, the monolayer of the cells was 'wounded' by removal of cells, generating a denuded area of 0.4-0.5 mm across. Regrowth of cells (wound healing) in the presence of α-TOS or α-TEA was assessed by following the kinetics of narrowing the denuded gap in the microscope equipped with a grid in the eyepiece and healing expressed as the 'rate of filling the gap' as the rate of healing in μm/h.

For the tube-forming activity of EAhy926 cells, formation of capillary-like structures in a 3-dimensional setting was assessed, essentially as described elsewhere (Albini, A., et al Inhibition of angiogenesis and vascular tumor growth by interferon-producing cells: A gene therapy approach. Am. J. Pathol. 156, 1381-1393 (2000)). In brief, 300 μl of cold Matrigel (BD Biosciences) was transferred using cold tips into each well in a 24-well plate. After solidification in the incubator, the surface of Matrigel was gently overlayed by a suspension of EAhy926 cells trypsinized from a proliferating culture, so that 200 μl of the complete cell media including the HAT supplement with $5\times10^5$ cells was added to each well. After 1-2 h in the incubator, the polygonal structures, made by a network of EAhy926 capillaries, established. The cells were treated by addition of MitoVES, added to the cell suspension just before it was transferred to the wells or after the tubes were established. Tube-forming activity was estimated by counting the number of complete capillaries interconnecting individual points of the polygonal structures in a selected field in a light microscope. Three fields in the central area of the well were chosen randomly in every well. The number of such capillaries in control cultures was considered 100%. For treated cultures, the number of complete capillaries was counted at various times after the onset of the experiment to obtain the kinetics of inhibition of tube-forming activity of EAhy926 cells.

Transmission Electron Microscopy.

Cultures to be subjected to transmission electron microscopy were prepared as previously described (Weber, T. et al. Mitochondria play a central role in apoptosis induced by α-tocopheryl succinate, an agent with anticancer activity. Comparison with receptor-mediated pro -apoptotic signaling. Biochemistry 42, 4277-4291 (2003)). Briefly, cultures of Jurkat cells were fixed by adding 2% glutaraldehyde (Agar Scientic, Essex, UK) in 0.1 M sucrose-sodium cacodylate-HCl buffer (pH 7.2; Sigma, St Louis, Mo., USA) and post-fixed in osmium (Johnson Matthey Chemicals, Roystone, UK). Thereafter, cells were pelleted in 2% agar prior to dehydration, staining with uranyl acetate (Sigma), dehydration and embedding in Epon-812 (Fluka A G, Buchs, Switzerland). Thin sections of cured blocks were cut with a diamond knife (DIATOME, Bienne, Switzerland), stained with lead-citrate (Sigma), examined and photographed in a JEOL 1230-EX electron microscope (Tokyo, Japan) at 100 kV.

Molecular Modeling—Complex II and MitoVES.

The crystal structure of mitochondrial respiratory membrane protein Complex II from porcine heart was obtained from the Brookhaven Protein Databank (code 1ZOY) (Sun F, Huo X, ZhaiY, Wang A, Xu J, Su D, Bartlam M, Rao Z. 2005. Crystal structure of mitochondrial respiratory membrane protein complex II. Cell 121:1043-1057). The Complex contains four proteins. Three subunits in this Complex, the iron-sulfur protein (Chain B), the large (Chain C) and small (Chain D) trans-membrane proteins are involved in the binding to UbQ. A BLAST search from the NCBI website revealed that the sequence identity between porcine and human Complex II is very high, 97% for the iron-sulfur protein, 90% for the large trans-membrane protein and 94% for the small trans-membrane protein.

The protein structure was prepared for docking using AutoDock Tools (Sanner M F (1999) Python: a programming language for software integration and development, J Mol Graphic Mod 17: 57-61) with the heteroatoms being removed first. Polar hydrogens were added to the structure and Kollman United Atom charges were used for the protein atoms. UbQ5 was built from the crystal structure coordinates of the bound UbQ (1ZOY) using InsightII (Accelrys, 2001). $MitoVE_{11}S$ was built from the crystal structure MOPHLB01 retrieved from the Cambridge Structural Database (Allen F H (2002) The Cambridge Structural Database: a quarter of a million crystal structures and rising. Acta Crystallogr B 58(Pt 3 Pt 1):380-388) by a sub-structure search for the ring system of α-TOS, again using InsightII. Both ligands were then prepared for docking by AutoDock Tools, which included merging non-polar hydrogens, assigning Gasteiger charges and defining the rotatable bonds.

Docking was performed using the Lamarckian Genetic Algorithm as implemented in Autodock 3.0.5. (Morris G M, Goodsell D S, Halliday R S, Huey R, Hart W E, Belew R K, Olson A J (1998) Automated docking using a Lamarckian genetic algorithm and empirical binding free energy function. J Comp Chem 19: 1639-1662); two docking grids were prepared. Both were 126×126×126 points with a grid pacing of 0.375 Å, with the first centred on Tyr173 (Chain B) in the $Q_P$ site and the second centered on Trp134 (Chain D) in the $Q_D$ site. Default parameters were used except for the following, which were increased due to the relatively high number of rotatable bonds present in the ligands of interest (UbQ5=16, α-TOS=17): —ga_run=250, ga_pop_size=250, ga_num_evals=10,000,000. Also, the parameter rmstol was increased to 2.5, to produce more manageable clusters during the analysis phase of the calculation. Each docking calculation took just over 49 h using a 2 GHz G5 PowerPC Macintosh. Analysis of results was performed using scripts provided with AutoDock and docked structures were visualized using Astex Viewer (Hartshorn M J (2002) AstexViewer™: An aid for structure-based drug design. J Computer Aided Mol Des 16: 871-881).

Example 1

MitoVES Selectively Kill Cancerous Cells

FIG. 2 shows that mitochondrially targeted redox-silent analog of vitamin E has a considerably higher apoptogenic effect against cancer cells and anti-cancer activity compared to its untargeted α-TOS counterpart, whilst maintaining its selectivity for cancer cells. In particular, $MitoVE_{11}S$ (Mito-α-TOS) was found to be up to 50-fold more apoptogenic than the prototypic α-TOS in cancer cells.

$IC_{50}$ values of α-TOS, VES4TPP and $MitoVE_{11}S$ (labelled "MitoVES") for different malignant and non-malignant cells are shown in Table V below.

TABLE V

| Cell type[a] | α-TOS | VES4TPP | MitoVES |
|---|---|---|---|
| Jurkat | 18 ± 3[b] | 21 ± 5 | 0.48 ± 0.1 |
| MM-BI | 26 ± 4 | n.d. | 1.4 ± 0.3 |
| Meso-2 | 29 ± 5 | 28 ± 6 | 2.4 ± 0.5 |
| Ist-Mes | 24 ± 5 | n.d. | 2.2 ± 0.3 |
| Ist-Mes-2 | 21 ± 3 | n.d. | 1.1 ± 0.25 |
| MCF-7 | 22 ± 4 | 19 ± 3 | 1.9 ± 0.5 |
| MDA-MB-453 | 28 ± 5 | n.d. | 3.3 ± 0.7 |
| HCT-116 | 31 ± 6 | n.d. | 2.8 ± 0.8 |
| AE-17 | 33 ± 5 | n.d. | 3.1 ± 0.7 |
| H9c2 | >100 | >100 | 54 ± 8 |
| HL-1 | >100 | >100 | 48 ± 6 |
| Met5A | 69 ± 8 | n.d. | 21 ± 4 |
| EAhy926[c] | >100 | n.d. | 32 ± 6 |
| | 9.5 ± 2.7 | n.d. | 0.7 ± 0.2 |

[a]Jurkat cells were treated at $0.5 \times 10^6$ per ml, other cell lines (except for EAhy926 cells) were treated at ~60% confluency.
[b]The $IC_{50}$ values are derived from viability curves using the MTT viability assay and are expressed μmol/l.
[c]The EAhy926 cells were treated at 100% confluency (top lines) or at ~50% confluency (bottom lines).

$IC_{50}$ values for various other MitoVES analogs and compounds are shown in Table VI below.

TABLE VI

| Analog | $IC_{50}$ |
|---|---|
| α-TOH[a] | >100[b] |
| α-TOS | 18 ± 3 |
| VE3S | ND |
| VE5S | ND |
| VE7S | ND |
| VE11S | 17.1 ± 4.2 |
| MitoVE3S | ND |
| MitoVE5S | ND |
| MitoVE7S | ND |
| MitoVE11S | 0.48 ± 0.1 |
| VES4TPP | 21 ± 5 |

[a]Jurkat cells were treated at $0.5 \times 10^6$ per ml and exposed to the analogs shown, added as EtOH solution.
[b]The $IC_{50}$ values are derived from viability curves using the MTT viability assay and are expressed in μmol/l.

The apoptosis assays of FIG. 2 show that $MitoVE_{11}S$ causes apoptosis selectively in malignant cells but not the normal equivalent cell types, with the exception of dividing endothelial cells.

The micrographs of α-TOS- and $MitoVE_{11}S$-treated Jurkat cells in panel J reveal typical hallmark signs of apoptosis.

Figure 3B:
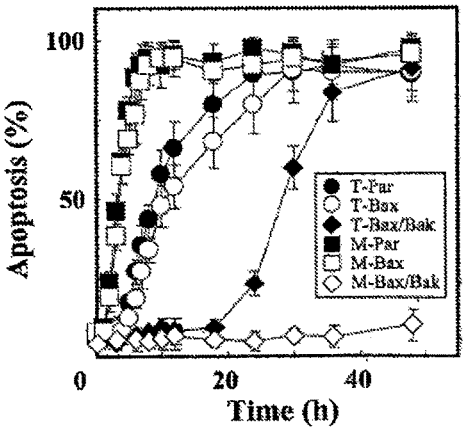

Interestingly, the apoptosis assay of FIG. 3B shows that $MitoVE_{11}S$ treatment of human Jurkat T-lymphoma cells induced apoptosis predominantly via the mitochondrial pathway because a Bax/Bak double knockout cell line proved extremely resistant to $MitoVE_{11}S$ and both of these BH3 only proteins are known to be required for mitochondrial outer membrane permeabilization during apoptosis via the intrinsic pathway.

It can also be gleaned from the apoptosis assay of FIG. 3B that $MitoVE_{11}S$ is a more potent and specific anticancer drug targeting death via the mitochondrial pathway. By comparison, α-TOS still mediates some level of killing in the Bax.Bak double deficient cells, suggesting that it can induced death via other pathways besides the mitochondrial one for apopotosis as well.

The results of Tables V and VI highlight the much greater potency of MitoVES in killing a range of cancer cell types, including lymphoma, mesothelioma, breast cancer and colon cancer, but not normal cells. In addition, the results suggest that chain length of the MitoVES is important probably for accessing down into the UbQ binding complex II site. The length of the carbon chain separating the TPP moiety from the TOS moiety is critical for activity and most likely reflects the ability of the TOS group to become inserted into the mitochondrial membrane deep enough to enter the UbQ sites on complex II.

Example 2

MitoVES Causes Apoptosis in Proliferating but not Arrested Endothelial Cells The results of FIG. 6 show that MitoVES ($MitoVE_{11}S$) causes apoptosis in proliferating but not arrested endothelial cells due to accumulation of ROS, thus revealing its potential as a potent anti-angiogenic agent. Hence, $MitoVE_{11}S$ is an effective inhibitor of angiogenesis and has direct anticancer effects by killing cancer cells via apoptosis.

Example 3

MitoVES Inhibits Angiogenesis In Vitro

The wound-healing, tube-forming and apoptosis assays of FIG. 7 shows that MitoVES ($MitoVE_{11}S$) inhibits angiogenesis in vitro, thus again affirming its potential as a potent anti-angiogenic agent.

As with α-TOS, $MitoVE_{11}S$ has a very potent anti-angiogenic activity in targeting and killing proliferating endothelial cells. However, $MitoVE_{11}S$ shows a surprising 5-fold greater potency as an antiangiogenic drug. For comparable levels of effects on the same endothelial cell types, about 5-10 micromolar $MitoVE_{11}S$ compared to about 25-50 micromolar α-TOS is needed. (The α-TOS level was taken from Lan-Feng Dong, Emma Swettenham, Johanna Eliasson, Xiu-Fang Wang, Mikhal Gold, Yasmine Medunic, Marina Stantic, Pauline Low, Lubomir Prochazka, Paul K. Witting, Jaroslav Turanek, Emmanuel T. Akporiaye, Stephen J. Ralph, and Jiri Neuzil, Vitamin E Analogues Inhibit Angiogenesis by Selective Induction of Apoptosis in Proliferating Endothelial Cells: The Role of Oxidative Stress, Cancer Res 2007; 67: (24). Dec. 15, 2007.)

Example 4

Complex II Genetically Deficient Mutant Cancer Cell Line is not Responsive to MitoVES Previous studies by the present inventors have shown that α-TOS induces ROS by interfering with the UbQ sites in the respiratory chain of Complex II. This example shows that a Complex II genetically deficient mutant cancer cell line is not responsive to MitoVES, thus confirming that MitoVES ($MitoVE_{11}S$) induces ROS by interfering with the UbQ sites in the respiratory chain of Complex II.

The effects of $MitoVE_{11}S$ treatment of a parental (B1), Complex II defective (B9) and Complex I-defective mutant (B10) Chinese hamster lung fibroblast cell lines were compared. In addition, a v-Harvey Ras expressing plasmid vector was used to transform those cell lines to the state of malignancy. Thus, the B1, B9 and B10 cell lines were transformed by stable transfection with GFP-H-Ras using the pEGFP-C3-H-Ras plasmid (Baysal B E, Ferrell R E, Willett-Brozick J E, Lawrence E C, Myssiorek D, Bosch A, van der Mey A, Taschner P E, Rubinstein W S, Myers E N, Richard C W 3rd, Cornelisse C J, Devilee P, Devlin B. Mutations in SDHD, a mitochondrial complex II gene, in hereditary paraganglioma. Science. 2000 Feb. 4; 287(5454): 848-51). Complex II in the Ras-transformed B9 cell line was reconstituted by transfecting with human (h) CybL (Albayrak T, Scherhammer V, Schoenfeld N, Braziulis E, Mund T, Bauer M K, Scheffler I E, Grimm S. The tumor suppressor cybL, a component of the respiratory chain, mediates apoptosis induction. Mol Biol Cell. 2003 August; 14(8):3082-96) cloned into the pEFIRES-Puro plasmid. RT-PCR documented the absence of the Chinese Hamster SDHCmRNA expression in the B9 derived cell line and the presence of hSDHC protein in $B9_{SDHC}$ expressing transformant cells (see FIG. 4A). The transfected cells were then subjected to clonal selection for those expressing the highest levels of H-Ras-EGFP (see FIG. 4B). The different ras-transformed cell lines were then exposed to the MitoVES analogue $MitoVE_{11}S$ and assessed for apoptosis efficacy, propensity to accumulate ROS and for SDH activity.

Figure 4C:
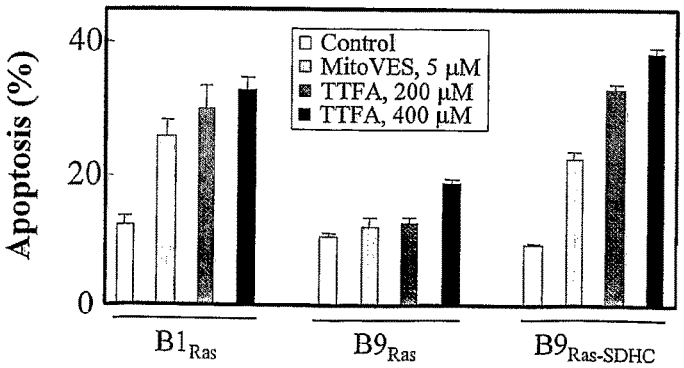

In FIG. 4C, it can be clearly seen that the Ras-transformed B9 cells with a defective Complex II in their mitochondria are much less sensitive to the Complex II targeting drugs TTFA or $MitoVE_{11}S$ compared to the Ras-transformed B1 cell line with a wild type Complex II expression and activity. Furthermore, reconstitution of Complex II function in the Ras-transformed B9 cells transfected to express the human SDHC protein restored the sensitivity of the cell line to the Complex II inhibitors, TTFA or $MitoVE_{11}S$. Hence, the evidence clearly identifies Complex II as the target site for both $MitoVE_{11}S$ and TTFA activity in inducing apoptosis in these cancer cells.

Example 5

MitoVES Targets the UbQ-Binding Pockets on Complex II

To rationalize the results that MitoVES interacts with Complex II via the UbQ-binding sites, the present inventors undertook a molecular modeling study using AutoDock (Morris G M, Goodsell D S, Halliday R S, Huey R, Hart W E, Belew R K, Olson A J (1998) Automated docking using a Lamarckian genetic algorithm and empirical binding free energy function. J Comp Chem 19: 1639-1662). The crystal structure of porcine heart mitochondrial CII has been reported (Sun F, Huo X, ZhaiY, Wang A, Xu J, Su D, Bartlam M, Rao Z. 2005. Crystal structure of mitochondrial respiratory membrane protein complex II. Cell 121:1043-1057). It exhibits a high sequence identity with human CII (95-97% for the individual subunits), therefore the present inventors used this structure (1ZOY) and the related structure (1ZP0) with the inhibitor TTFA bound as the basis for modeling study. As shown in FIG. 5, the docking experiment produced the bound structure as shown in the space filling model of Complex II, with $MitoVE_{11}S$ identified as a stick figure structure. The surface of Chain B (iron-sulfur protein) of Complex II and the surfaces of Chains C and D (the transmembrane section) are shown but Chain A (flavoprotein-succinate reductase) is not shown.

The predicted position of $MitoVE_{11}S$ is shown as the sticks and the translucent grey box is drawn to indicate approximately where the membrane bilayer would exist. The model identifies the position proposed for $MitoVE_{11}S$ binding and docking into the Qp ubiquinone site of Complex II with the triphenylphosphonium ion protruding out on the membrane surface sitting in the mitochondrial matrix near the base of the structure of the SDH enzyme head group outside.

Example 6

MitoVES is an Efficient Drug for Killing Breast Cancer Stem Cells

A recent important discovery in cancer therapy has been that cancer stem cells exist which can be the source for repopulating a tumour. This also highlights the difficulty with treating cancers, because any treatment that kills the bulk of a tumour, but leaves the stem cells alive in the body will fail because the tumour will regrow (Lou and Dean, Oncogene 2007). Cancer stem cells are also highly significant targets because they are commonly resistant to therapy (O'Brien et al. 2008, Li et al., 2008) and are drug resistant, expressing the Multi Drug Resistance (MDR)/ABC transporter glycoproteins on their cell membranes, involved in preventing chemotherapeutic drugs from accumulating in the cancer stem cells. The cancer stem cells have also been found to be radiation resistant because they have greater DNA damage repair capacity (Neuzil et al., 2007 BBRC; Eyler and Ricj, 2008).

Cancer stem cells have been enriched by selective methods including purification based on their propensity to exclude dyes such as Hoechst 33342 providing a "side population" of cells when gated by fluorescence activated cell sorting (Patrawala L et al 2005, Wu and Alman 2008). Another means for enriching for cancer stem cell populations involves the growth in culture of spheroids from tumour cells. This method has been shown to enrich for higher percentages of tumour initiating cells within such cultures (Grimshaw et al., 2008) with many of the properties of cancer stem cells, including radiation resistance (Phillips T M et al., 2007). Based on analyses of gene expression and protein marker expression on the cancer stem cell enriched populations, these cell types have become more characterised. Among the marker genes and proteins expressed by cancer stem cells are increased levels of the Notch/wnt/beta-catenin signalling pathway, ABC transporters, CD133 high, CD44 high and low levels of CD24 surface markers. These cells, based on their marker expression also correlate closely with the more "basal" tumour cell phenotypes isolated from aggressively lethal malignancies and analysed by gene expression profiling (for example, see Sorlie T et al., PNAS, 2001; review in Sotiriou and Pusztai, 2008).

Given our understanding of the properties of cancer stem cells or tumour initiating cells, it becomes imperative that a drug is found that targets these cell types and kills them, thereby preventing tumour regrowth. Preferably, this drug is selective and does not significantly affect normal stem cells or other normal cell types. One such drug that has been described is parthenolide, a sesquiterpene lactone derived from the Feverfew plant, which has been found to selectively kill leukemic stem cells (Guzman M L et al., 2005). Another similar drug was the compound 4-benzyl, 2-methyl, 1,2,4-thiadiazolidine, 3,5 dione (TDZD-8, Guzman, M L et al, 2007). However, these compounds proved not to be very effective against other types of cancer such as solid tumours.

The present inventors made the surprising discovery that MitoVES was a highly effective drug for killing populations of the human breast cancer cell line, MCF7, enriched for cancer stem cells by growth as mammospheres (MS) in culture. The results in FIG. 8 show the morphology of the adherent MCF7 cells and the corresponding MS cells, as well as analyses for expression of a number of markers for cancer stem cells. They found that adherent MCF7 cells, although sensitive to killing by α-TOS, were more so to the drug, MitoVES. However, these cells were not responsive to parthenolide, the agent previously reported to kill cancer stem cells, particularly leukemia stem cells. In addition, MS cells derived from MCF7 cells showed low levels of sensitivity to parthenolide and were resistant to α-TOS. However, the MS cells, with their high levels of sternness (indicated by cancer stem cell markers) were surprisingly very sensitive to the drug MitoVES, such that there was >90% apoptosis within 5-6 h after adding the drug to the MS cells. The inventors also found that α-TOS caused significant production of ROS in adherent MSFT cells but much lower levels in the MS cells. However, MitoVES caused greater ROS accumulation in adherent MCF7 cells than did α-TOS, and even higher levels in the MS cells. Further, the shorter chain homologues of MitoVES were less efficient than $MitoVE_{11}S$ at promoting ROS accumulation, both in the adherent MCF7 cells and in the corresponding MS cultures. These findings identify $MitoVE_{11}S$ as a compound with very high propensity to kill cancer stem cells, as shown for the MS cultures derived from the human breast cancer cell line MCF7.

The inventors also found that MitoVES was a highly effective anti-cancer drug in vivo. For this purpose, the transgenic FVB/N c-neu mice that form spontaneous ductal breast carcinomas due to high level of expression of the oncogene, HER2 were used as a cancer model. The inventors found that MitoVES treatment completely blocked progression of breast cancer tumours arising in these animals (FIG. 9) at concentrations some 10-fold lower than those needed for corresponding activity of α-TOS. Importantly, no obvious sign of toxicity was observed in any of the treated animals.

The present inventors have shown that untargeted mitocans can be modified by addition of a cationic group that presumably anchors them in the luminal leaflet of the inner mitochondrial membrane, thus maximizing their activity. This is epitomized by mitochondrially targeted analogs of vitamin E that show a considerably higher apoptogenic effect against cancer cells including tumor-initiating cells, and anti-cancer activity compared to their untargeted counterparts, whilst maintaining their selectivity for cancer cells.

In particular, the experimental examples indicate that:

1) MitoVES (MitoVE$_{11}$S) is surprisingly much greater in potency than α-TOS, ~up to 50 fold more active on cancer cells in killing them selectively than α-TOS;

2) MitoVES will, as a result of 1), be much less toxic on normal cells with the improved specificity;

3) MitoVES is more specific in inducing the mitochondrial pathway for cell death than α-TOS;

4) As with α-TOS, MitoVES has a very potent antiangiogenic activity in targeting and killing proliferating endothelial cells, but MitoVES (MitoVES) shows a surprising 5-fold greater potency as an antiangiogenic drug than α-TOS; and 5) MitoVES is likely to have very broad application in cancer therapy, in view it killing mesothelioma, breast cancer, colon cancer, lymphoma cell lines and cancer stem cells.

The foregoing embodiments are illustrative only of the principles of the invention, and various modifications and changes will readily occur to those skilled in the art. The invention is capable of being practiced and carried out in various ways and in other embodiments. It is also to be understood that the terminology employed herein is for the purpose of description and should not be regarded as limiting.

The term "comprise" and variants of the term such as "comprises" or "comprising" are used herein to denote the inclusion of a stated integer or stated integers but not to exclude any other integer or any other integers, unless in the context or usage an exclusive interpretation of the term is required.

Any reference to publications cited in this specification is not an admission that the disclosures constitute common general knowledge in Australia or elsewhere.

LIST OF REFERENCES FOR TABLES II-IV AND FOR EXAMPLE 6

Arya P, Alibhai N, Qin H, Burton G W, Batist G, You S X and Alaoui-Jamali M A (1998) Design and synthesis of analogues of vitamin E: antiproliferative activity against human breast adenocarcinoma cells. Bioorg Med Chem Lett 8:2433-2438.

Birringer M, EyTina J H, Salvatore B A and Neuzil J (2003) Vitamin E analogues as inducers of apoptosis: Structure-function relationship. Br J Cancer 88:1948-1955.

Eyler, C E and Ricj, J N (2008) Survival of the Fittest: Cancer Stem Cells in Therapeutic Resistance and Angiogenesis. J Clin Oncol. June 1; 26(17):2839-2845

Farnie G, Clarke R B, Spence K, Pinnock N, Brennan K, Anderson N G, Bundred N J. (2007) Novel cell culture technique for primary ductal carcinoma in situ: role of Notch and epidermal growth factor receptor signaling pathways. J Natl Cancer Inst. April 18; 99(8):616-27.

Galli F, Stabile A M, Betti M, Conte C, Pistilli A, Rende M, Floridi A and Azzi A (2004) The effect of α- and γ-tocopherol and their carboxyethyl hydroxychroman metabolites on prostate cancer cell proliferation. Arch Biochem Biophys 423:97-102.

Grimshaw M J, Cooper L, Papazisis K, Coleman J A, Bohnenlcamp H R, Chiapero-Stanke L, Taylor-Papadimitriou J, Burchell J M. (2008) Mammosphere culture of metastatic breast cancer cells enriches for tumorigenic breast cancer cells. Breast Cancer Res.; 10(3):R52. Epub 2008 Jun. 9.

Guthrie N, Gapor A, Chambers A F and Carroll K K (1997) Inhibition of proliferation of estrogen receptor-negative MDA-MB-435 and -positive MCF-7 human breast cancer cells by palm oil tocotrienols and tamoxifen, atone and in combination. J Nutr 127: 544S-548S.

Guzman M L, Li X, Corbett C A, Rossi R M, Bushnell T, Liesveld J L, Hebert J, Young F, Jordan C T. (2007) Rapid and selective death of leukemia stem and progenitor cells induced by the compound 4-benzyl, 2-methyl, 1,2,4-thiadiazolidine, 3,5 dione (TDZD-8). Blood. December 15; 110 (13):4436-44.

Guzman M L, Rossi R M, Karnischky L, Li X, Peterson D R, Howard D S, Jordan C T. (2005) The sesquiterpene lactone parthenolide induces apoptosis of human acute myelogenous leukemia stem and progenitor cells. Blood. June 1; 105(11):4163-9.

He L, Mo H, Hadisusilo S, Qureshi AA and Elson C E (1997) Isoprenoids suppress the growth of murine B16 melanomas in vitro and in vivo. J Nutr 127:668-674.

He D Y, Yu L, Yu C A. (1994) Protein ubiquinone interaction. Synthesis and biological properties of 5-alkyl ubiquinone derivatives. J Biol. Chem. November 11; 269 (45):27885-8.

Kogure K, Hama S, Kisaki M, Takemasa H, Tokumura A, Suzuki I and Fukuzawa K (2004) Structural characteristic of terminal dicarboxylic moiety required for apoptogenic activity of α-tocopheryl esters. Biochim Biophys Acta 1672: 93-99.

Kogure K, Manabe S, Suzuki I, Tokumura A and Fukuzawa K (2005) Cytotoxicity of α-tocopheryl succinate, malonate and oxalate in normal and cancer cells in vitro and their anti-cancer effects on mouse melanoma in vivo. J Nutr Sci Vitaminol 51:392-397.

Li X, Lewis M T, Huang J, Gutierrez C, Osborne C K, Wu M F, Hilsenbeck S G, Pavlick A, Zhang X, Chamness G C, Wong H, Rosen J, Chang J C. (2008) Intrinsic resistance of tumorigenic breast cancer cells to chemotherapy. J Natl Cancer Inst. May 7; 100(9):672-9.

Lou H, Dean M. (2007) Targeted therapy for cancer stem cells: the patched pathway and ABC transporters. Oncogene. February 26; 26(9):1357-60.

Makishima M, Umesono K, Shudo K, Naoe T, Kishi K and Honma Y (1998) Induction of differentiation in acute promyelocytic leukemia cells by 9-cis retinoic acid α-tocopherol ester (9-cis tretinoin tocoferil). Blood 91:4715-4726.

Munteanu A, Zingg J M, Ogru E, Libinaki R, Gianello R, West S, Negis Y and Azzi (2004) Modulation of cell proliferation and gene expression by α-tocopheryl phosphates: relevance to atherosclerosis and inflammation. Biochem Biophys Res Commun 318:311-316.

Nesaretnam K, Stephen R, Dils R and Darbre P (1998) Tocotrienols inhibit the growth of human breast cancer cells irrespective of estrogen receptor status. Lipids 33:461-469.

Neuzil J, Weber T, Gellert N, Weber C (2001) Selective cancer cell killing by α-tocopheryl succinate. Br J Cancer 84:87-89.

Neuzil J, Weber T, Schroder A, Lu M, Ostermann G, Gellert N, Mayne G C, Olejnicka B, Negre-Salvayre A, Sticha M, Coffey R J, Weber C (2001) Induction of apoptosis in cancer cells by α-tocopheryl succinate: Molecular pathways and structural requirements. FASEB J 15:403-415.

Neuzil J, Stantic M, Zobalova R, Chladova J, Wang X, Prochazka L, Dong L, Andera L, Ralph S J. (2007) Tumour-initiating cells vs. cancer 'stem' cells and CD133: what's in the name? Biochem Biophys Res Commun. April 20; 355 (4):855-9.

O'Brien C S, Farnie G, Howell S J, Clarke R B. (2008) Are stem-like cells responsible for resistance to therapy in breast cancer? Breast Dis.; 29:83-9.

Phillips T M, McBride W H, Pajonk F. (2006) The response of CD24(−/low)/CD44+ breast cancer-initiating cells to radiation. J Natl Cancer Inst. December 20; 98(24): 1777-85.

Shah S J and Sylvester P W (2005) γ-Tocotrienol inhibits neoplastic mammary epithelial cell proliferation by decreasing Akt and nuclear factor KB activity. Exp Biol Med 230: 235-241.

Shiau C W, Huang J W, Wang D S, Weng J R, Yang C C, Lin C H, Li C, Chen C S (2006) alpha-Tocopheryl succinate induces apoptosis in prostate cancer cells in part through inhibition of Bcl-xL/Bcl-2 function. J Biol Chem 281: 11819-11825.

Shun M C, Yu W, Gapor A, Parsons R, Atkinson J, Sanders B G and Kline K (2004) Pro -apoptotic mechanisms of action of a novel vitamin E analog (α-TEA) and a naturally occurring form of vitamin E (δ-tocotrienol) in MDA-MB-435 human breast cancer cells. Nutr Cancer 48:95-105.

Sørlie T, Perou C M, Tibshirani R, Aas T, Geisler S, Johnsen H, Hastie T, Eisen M B, van de Rijn M, Jeffrey S S, Thorsen T, Quist H, Matese J C, Brown P 0, Botstein D, Eystein Lønning P, Børresen-Dale A L. (2001) Gene expression patterns of breast carcinomas distinguish tumor subclasses with clinical implications. Proc Natl Acad Sci USA. September 11; 98(19):10869-74.

Sotiriou C, Pusztai L. (2009) Gene-expression signatures in breast cancer. N Engl J. Med. February 19; 360(8):790-800.

Tomic-Vatic A, EyTina J H, Chapmann J M, Mandavian E, Neuzil J and Salvatore B A (2005) Vitamin E amides, a new class of vitamin E analogues with enhanced pro-apoptotic activity. Int J Cancer 117:118-193.

Vraka P S, Drouza C, Rikkou M P, Odysseos A D and Keramidas A D (2006) Synthesis and study of the cancer cell growth inhibitory properties of α-, γ-tocopheryl and γ-tocotrienyl 2-phenylselenyl succinates. Bioorg Med Chem 14: 2684-2696.

Yano Y, Satoh H, Fukumoto K, Kumadaki I, Ichikawa T, Yamada K, Hagiwara K and Yano T (2005) Induction of cytotoxicity in human lung adenocarcinoma cells by 6-O-carboxy-propyl-α-tocotrienol, a redox-silent derivative of α-tocotrienol. Int J Cancer 115:839-846.

The invention claimed is:

1. A compound [for inducing death of a cancerous cell, said compound comprising: a pro-oxidant moiety for (i) generating reactive oxygen species within mitochondria of the cancerous cell, (ii) inducing apoptosis of the cancerous cell, and (iii) interacting with mitochondrial complex II of the cancerous cell, wherein the pro-oxidant moiety comprises a vitamin E analogue comprising a functional domain at position C6 of a substituted chromanol ring that is capable of interacting with a Qp ubiquinone binding site of mitochondrial complex II, a domain that includes the substituted chromanol ring, and a hydrophobic domain comprising an at least seven-carbon long aliphatic chain; and a delivery moiety for delivering the pro-oxidant moiety to the mitochondria of the cancerous cell and for correctly positioning the functional domain for interaction with the Qp ubiquinone binding site, wherein the delivery moiety comprises a delocalized lipophilic triphenylphosphonium cation and said vitamin E analogue is] selected from the group consisting of [α-tocopheryl succinate, α-tocopheryl maleate, α-tocopheryl maleyl amide, and 2,5,7,8-tetramethyl-2R-(4R,8R,12-trimethyltridecyl)-chroman-6-yloxyacetic acid (α-tocopheryloxyacetic acid)]

*MitoVE$_7$S*

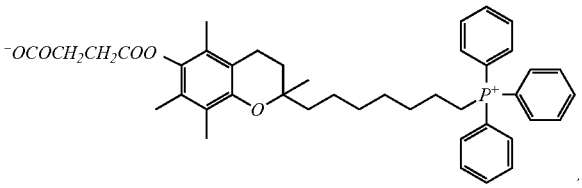

*MitoVE$_9$S*

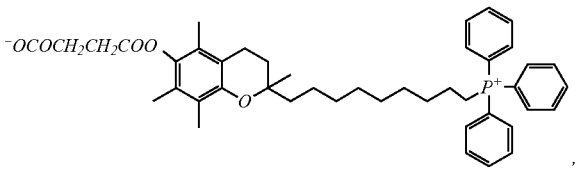

MitoVE$_{11}$S

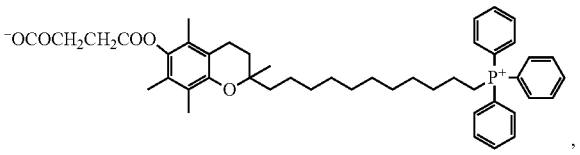

*MitoVE$_{11}$AE*

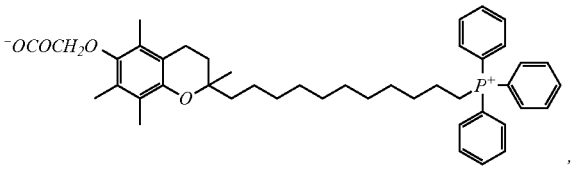

TPP-α-TOS

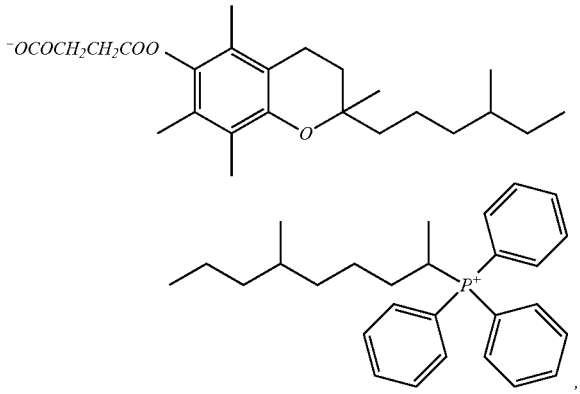

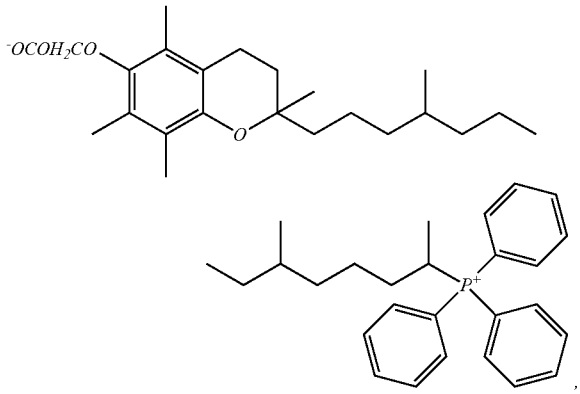

*triphenylphosphonium tagged 2,5,7,8-tetramethyl-2R-(4R, 8R,12-trimethyltridecyl)-chroman-6-yloxyacetic acid (triphenylphosphonium tagged α-tocopheryloxyacetic acid), and a derivative of any of the foregoing;*

*wherein said derivative has a functional domain substituted at position C6 of the chromanol ring of the compound that comprises a functional domain group selected from the group consisting of an ether, ester, amide, dissociated carboxylic acid, and hydrophilic head group comprising a dissociated acid, a charged ammonium group, or both;*

*and a physiologically acceptable salt of any of the foregoing.*

[2. The compound of claim 1, wherein the vitamin E analogue is α-tocopheryl succinate (α-TOS).]

[3. A pharmaceutical or veterinary composition comprising the compound of claim 1, or a physiologically acceptable salt thereof, and a physiologically acceptable carrier.]

[4. A method of inducing the death of a cancerous cell, said method comprising the step of administering to said cancerous cell or a subject having said cancerous cell a therapeutically effective amount of the compound according to claim 1.]

[5. The compound of claim 1, wherein the functional domain is selected from the group consisting of an ether, ester and amide substituted at position C6 of the chromanol ring.]

[6. The compound of claim 1, wherein the aliphatic chain comprises an 11 carbon long aliphatic chain.]

[7. The pharmaceutical or veterinary composition of claim 3, wherein the pro-oxidant moiety is a vitamin E analogue selected from the group consisting of α-tocopheryl succinate, α-tocopheryl maleate and α-tocopheryl maleyl amide, and the carrier is a transdermally applicable cream.]

[8. The pharmaceutical or veterinary composition of claim 3, wherein the pro-oxidant moiety is α-tocopheryloxyacetic acid and the carrier is suited for oral administration.]

*9. The compound of claim 1, wherein the compound is MitoVE$_7$S or a physiologically acceptable salt thereof.*

*10. The compound of claim 1, wherein the compound is MitoVE$_9$S or a physiologically acceptable salt thereof.*

*11. The compound of claim 1, wherein the compound is MitoVE$_{11}$S or a physiologically acceptable salt thereof.*

*12. The compound of claim 1, wherein the compound is MitoVE$_{11}$AE or a physiologically acceptable salt thereof.*

*13. The compound of claim 1, wherein the compound is TPP-α-TOS or a physiologically acceptable salt thereof.*

*14. A pharmaceutical or veterinary composition comprising the compound of claim 1, or a physiologically acceptable salt thereof, and a physiologically acceptable carrier.*

*15. The pharmaceutical or veterinary composition of claim 14, wherein the carrier is a cream.*

*16. The pharmaceutical or veterinary composition of claim 14, wherein the carrier is suited for oral administration.*

*17. A method of inducing death of a cancerous cell, said method comprising the step of administering to said cancerous cell or a subject having said cancerous cell a therapeutically effective amount of the compound according to claim 1, or a physiologically acceptable salt thereof.*

*18. The method of claim 17, wherein said method is used to treat cancer in the subject.*

*19. The compound of claim 1, wherein the compound is triphenylphosphonium tagged 2,5,7,8-tetramethyl-2R-(4R, 8R,12-trimethyltridecyl)-chroman-6-yloxyacetic acid (triphenylphosphonium tagged α-tocopheryloxyacetic acid) or a physiologically acceptable salt thereof.*

*20. The compound of claim 1, wherein the derivative is a maleate derivative of MitoVE$_{11}$S or a physiologically acceptable salt thereof.*

*21. The compound of claim 1, wherein the derivative is a maleyl amide derivative of MitoVE$_{11}$S or a physiologically acceptable salt thereof.*

*22. The compound of claim 1, wherein the derivative is a maleate derivative of TPP-α-TOS or a physiologically acceptable salt thereof.*

*23. The compound of claim 1, wherein the derivative is a maleyl amide derivative of TPP-α-TOS or a physiologically acceptable salt thereof.*

*24. A compound of Formula (I), or a physiologically acceptable salt thereof:*

*(I)*

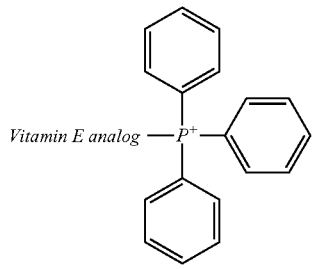

*wherein the compound is selected from the group consisting of*

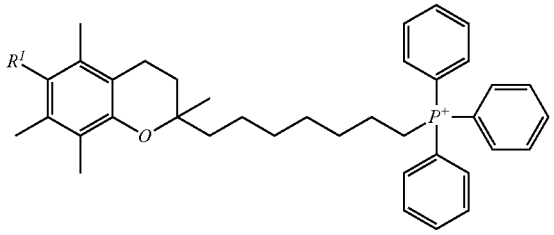

,

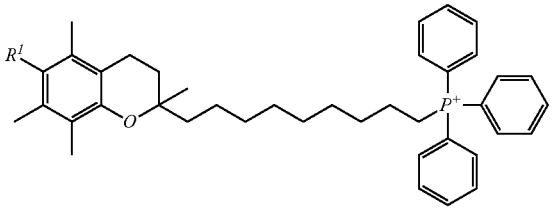

,

*wherein $R^1$ comprises a hydrophilic head group comprising a dissociated acid, an ammonium group, or both, and is linked to the chromanol ring through an ester bond, an amide bond, or an ether bond.*

*25. A compound of Formula (I), or a physiologically acceptable salt thereof:*

*(I)*

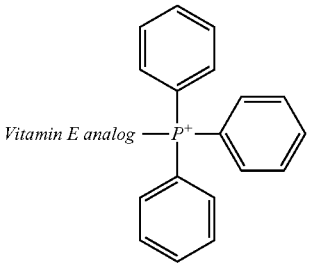

,

*wherein the compound is selected from the group consisting of*

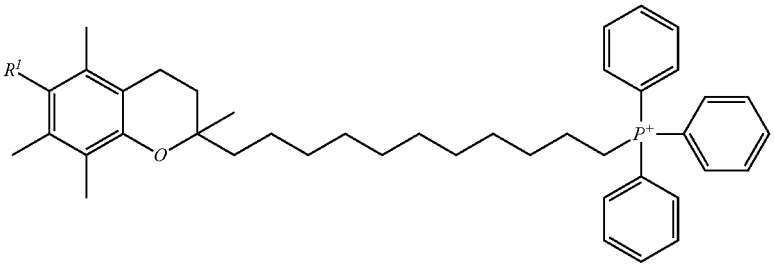

, *and*

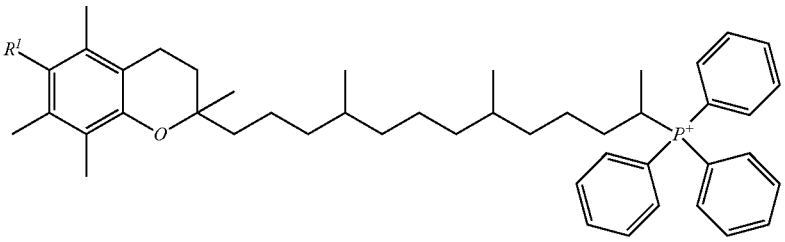

;

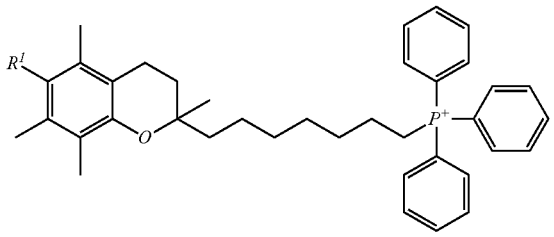
,
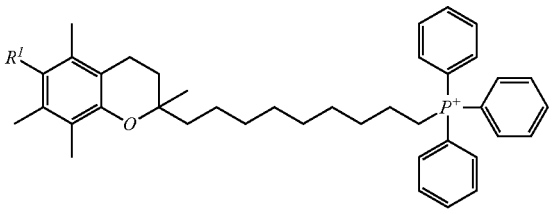
,
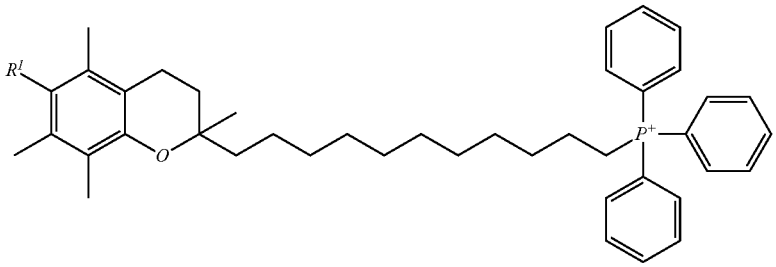
, *and*
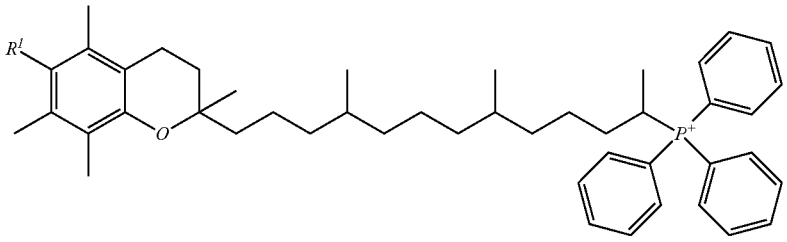
;
*wherein $R^1$ comprises a carboxylate or ammonium group, and is linked to the chromanol ring through an ester bond, an amide bond, or an ether bond.*
* * * * *